(12) United States Patent
Grunewald et al.

(10) Patent No.: US 10,585,204 B2
(45) Date of Patent: Mar. 10, 2020

(54) RELAXATION TIME ESTIMATION IN SURFACE NMR

(71) Applicant: VISTA CLARA INC., Mukilteo, WA (US)

(72) Inventors: Elliot D. Grunewald, Seattle, WA (US); David O. Walsh, Mukilteo, WA (US)

(73) Assignee: VISTA CLARA INC., Mukilteo, WA (US)

( * ) Notice: Subject to any disclaimer, the term of this patent is extended or adjusted under 35 U.S.C. 154(b) by 873 days.

(21) Appl. No.: 15/042,932

(22) Filed: Feb. 12, 2016

(65) Prior Publication Data
US 2016/0216395 A1 Jul. 28, 2016

Related U.S. Application Data

(63) Continuation-in-part of application No. 13/750,984, filed on Jan. 25, 2013, now Pat. No. 9,599,688.
(Continued)

(51) Int. Cl.
| | | |
|---|---|---|
| *G01V 3/14* | (2006.01) | |
| *G01N 24/08* | (2006.01) | |
| *G01R 33/44* | (2006.01) | |
| *G01R 33/341* | (2006.01) | |

(52) U.S. Cl.
CPC .............. *G01V 3/14* (2013.01); *G01N 24/081* (2013.01); *G01R 33/448* (2013.01); *G01R 33/341* (2013.01); *G01R 33/445* (2013.01)

(58) Field of Classification Search
CPC .... A61B 5/0263; G01N 24/081; G01N 24/08; G01N 24/082; G01N 24/085;
(Continued)

(56) References Cited

U.S. PATENT DOCUMENTS

| | | | | |
|---|---|---|---|---|
| 4,695,799 A | * | 9/1987 | Hardy .................. | G01R 33/446 324/307 |
| 5,019,784 A | * | 5/1991 | Garwood ............. | G01R 33/446 324/307 |

(Continued)

*Primary Examiner* — Steven L Yeninas
(74) *Attorney, Agent, or Firm* — Amin, Turocy & Watson, LLP

(57) ABSTRACT

Technologies including NMR relaxation time estimation methods and corresponding apparatus are disclosed. Example techniques may include performing at least one single-pulse acquisition sequence, the single-pulse acquisition sequence comprising transmitting a single modulated pulse with a surface coil, wherein the phase, frequency, or amplitude of the single modulated pulse is varied during the single modulated pulse, and wherein the single modulated pulse excites a transverse magnetization component within a subsurface fluid. The resulting NMR signal may be recorded on at least one receiving device, including recording the NMR signal associated with the transverse magnetization component excited by the single modulated pulse. Processing techniques may be applied in which recorded NMR response data are used to estimate NMR properties and the relaxation times $T_1$ and $T_2^*$ as a function of position as well as one-dimensional and two-dimension distributions of $T_1$ versus $T_2^*$ as a function of subsurface position.

22 Claims, 15 Drawing Sheets

Related U.S. Application Data

(60) Provisional application No. 61/591,643, filed on Jan. 27, 2012.

(58) Field of Classification Search
CPC .... G01R 33/32; G01R 33/341; G01R 33/445; G01R 33/448; G01R 33/3415; G01R 33/4608; G01R 33/4616; G01V 3/26; G01V 3/265; G01V 3/28; G01V 3/32
USPC .......................... 324/303, 307–315, 323–347
See application file for complete search history.

(56) References Cited

U.S. PATENT DOCUMENTS

| | | | |
|---|---|---|---|
| 5,160,888 A * | 11/1992 | Laukien | G01R 33/3808 324/309 |
| 6,160,398 A | 12/2000 | Walsh | |
| 6,166,541 A * | 12/2000 | Smith | G01R 33/3607 324/300 |
| 6,518,757 B1 * | 2/2003 | Speier | G01N 24/081 324/303 |
| 7,466,128 B2 | 12/2008 | Walsh | |
| 7,986,143 B2 | 7/2011 | Walsh | |
| 8,581,587 B2 | 11/2013 | Walsh | |
| 2004/0017193 A1 * | 1/2004 | Speier | G01N 24/081 324/303 |
| 2006/0186882 A1 * | 8/2006 | Walsh | G01R 33/3415 324/309 |
| 2010/0026299 A1 * | 2/2010 | King | G01R 33/3415 324/309 |
| 2011/0109311 A1 | 5/2011 | Walsh | |
| 2013/0187647 A1 | 7/2013 | Walsh | |
| 2013/0193969 A1 | 8/2013 | Grunewald | |
| 2014/0009148 A1 | 1/2014 | Walsh | |
| 2016/0291191 A1 * | 10/2016 | Fukushima | G01R 33/3415 |

* cited by examiner

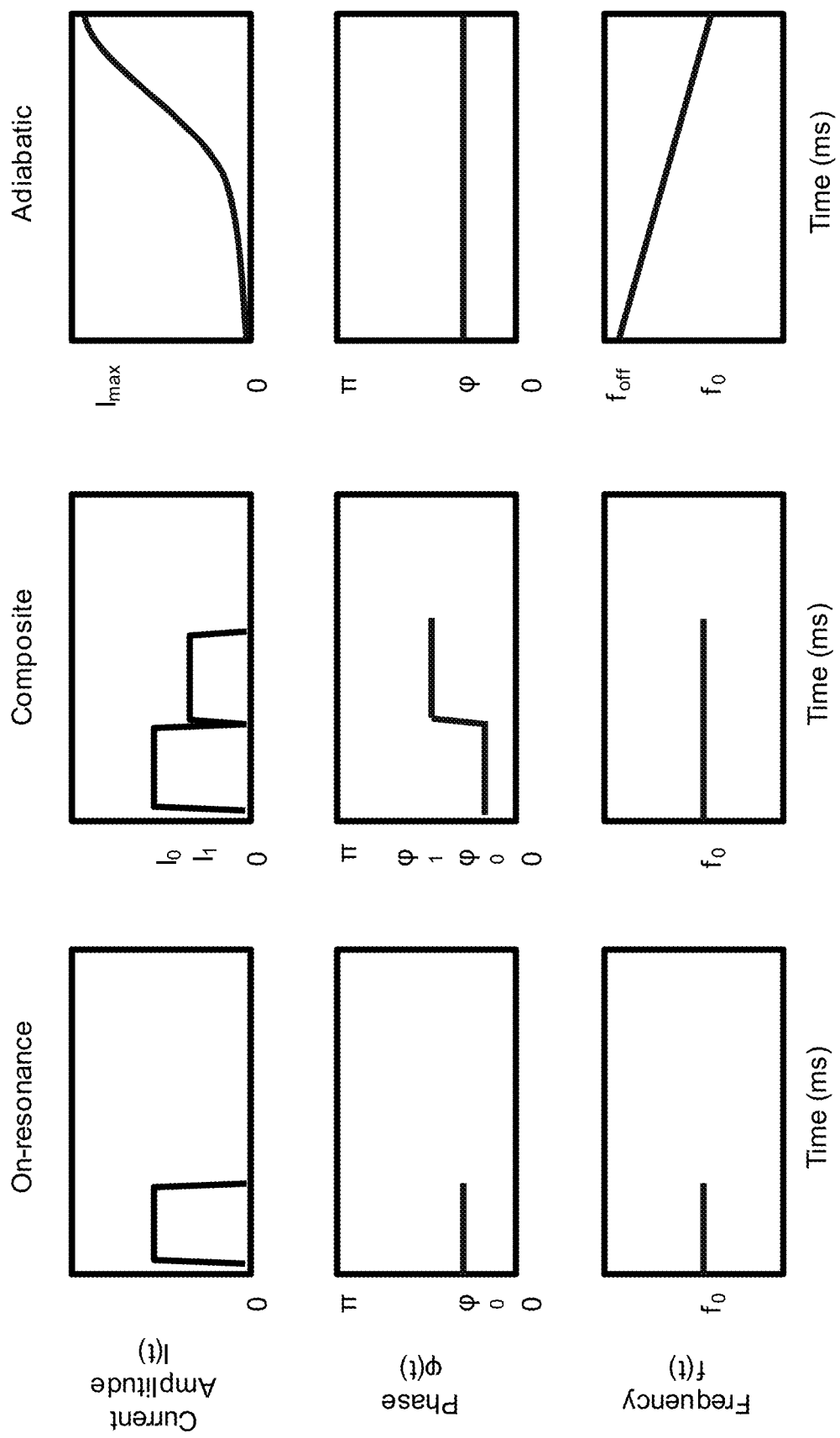

FIG. 10A
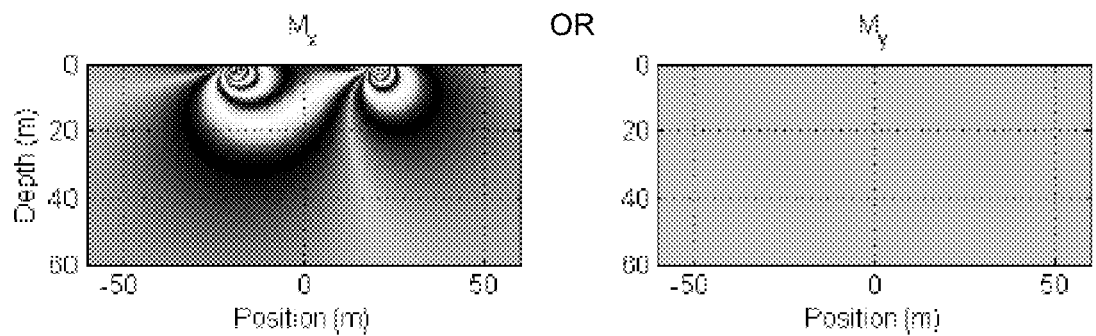
FIG. 10B
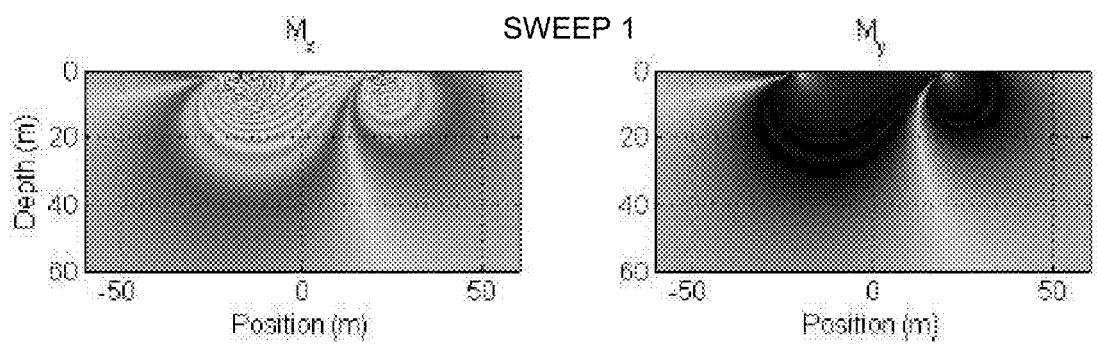
FIG. 10C
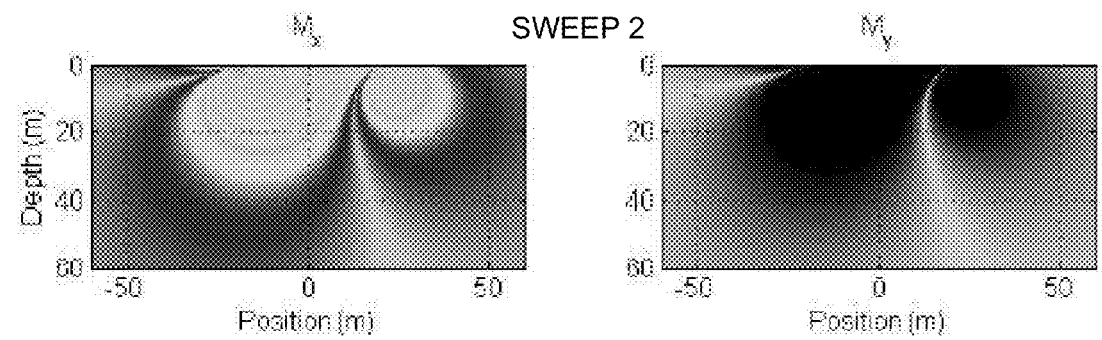
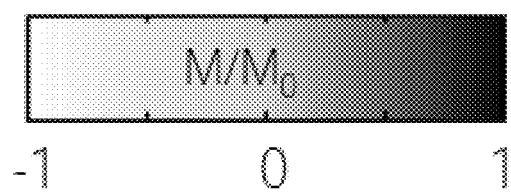

RELAXATION TIME ESTIMATION IN SURFACE NMR

CROSS REFERENCE TO RELATED APPLICATIONS

This is a continuation in part of U.S. patent application Ser. No. 13/750,984, filed on 25 Jan. 2013, entitled "RELAXATION TIME ESTIMATION IN SURFACE NMR," which is a nonprovisional claiming priority of U.S. Provisional Patent Application No. 61/591,643, filed on 27 Jan. 2012, entitled "RELAXATION TIME ESTIMATION IN SURFACE NMR." The contents of the prior applications are incorporated herein by reference in their entirety.

STATEMENT OF GOVERNMENT SUPPORT

This invention was made in part with Government support under Agreement DE-SC0013293 awarded by the US Department of Energy. The Government has certain rights in this invention.

FIELD OF THE INVENTION

The field of the invention is surface Nuclear Magnetic Resonance (NMR) technologies to measure NMR properties of subsurface fluids and formations, and to use measured NMR properties to estimate other physical properties of the subsurface.

BACKGROUND

NMR systems have been in use for many years and can be used to provide imaging and/or analysis of a sample being tested. For example, U.S. Pat. Nos. 6,160,398, 7,466,128, 7,986,143, U.S. patent application Ser. No. 12/914,138 and U.S. patent application Ser. No. 13/104,721 describe a variety of NMR technologies, and are incorporated herein by reference. Various different types of NMR include medical NMR, often referred to as Magnetic Resonance Imaging (MM), and surface NMR for measuring properties of earth formations. While there is some overlap in the technologies that may be applied in MM and surface NMR, the samples being measured and the environments in which measurements are performed are different, leading to many differences in the technologies applied.

In general, surface NMR measurement involves utilizing or generating a static magnetic field within a sample volume, emitting one or more electromagnetic pulses into the sample volume, and detecting NMR responses from the sample volume. In some cases, surface NMR measurement involves emitting multiple electromagnetic pulses in rapid succession and measuring the NMR responses between the electromagnetic pulses. The measured NMR responses provide useful information about the sample volume.

Surface NMR measurements may be used to detect, for example, the abundance of hydrogen contained within an underground sample volume, and NMR relaxation times within a sample. Detected hydrogen abundance and NMR relaxation times may be used to characterize many properties of fluid-bearing formations underground, such as the porosity, total quantity of fluids, fluid composition, pore size, and permeability of the sample. Three types of relaxation times of interest are referred to in the art as $T_2^*$, $T_2$, and $T_1$.

There is a need in the art for better surface NMR measurement apparatus and methods. In particular, improved technologies for estimating NMR relaxation times as described herein will provide better characterization of fluid-bearing formations underground.

SUMMARY

Technologies applicable to NMR relaxation time estimation are disclosed. NMR relaxation time estimation may comprise performing surface NMR measurement methods according to this disclosure, and using resulting NMR data to estimate relaxation times and formation properties.

Some example surface NMR measurement methods may comprise generating a set of multi-pulse acquisition sequences, each multi-pulse acquisition sequence comprising a preparatory pulse, wherein said preparatory pulse may be substantially identical in each of the multi-pulse acquisition sequences in the set. The preparatory pulses in the pulse sequences may comprise on-resonance pulses, adiabatic pulses, and/or composite pulses.

Each multi-pulse acquisition sequence may further comprise one or more ordered subsequent pulses following the preparatory pulse. A pulse moment of an ordered subsequent pulse in at least one of the multi-pulse acquisition sequences in the set may be different from a pulse moment of a same ordered subsequent pulse in at least one other of the multi-pulse acquisition sequences in the set.

Some example surface NMR measurement methods may comprise performing at least one single-pulse acquisition sequence, the single-pulse acquisition sequence comprising transmitting a single modulated pulse with a surface coil, wherein the phase, frequency, or amplitude of the single modulated pulse is varied during the single modulated pulse, and wherein the single modulated pulse excites a transverse magnetization component within a subsurface fluid. The resulting NMR signal may be recorded on at least one receiving device, including recording the NMR signal associated with the transverse magnetization component excited by the single modulated pulse.

Example methods may furthermore comprise using NMR response data produced from the set of multi-pulse acquisition sequences to estimate NMR relaxation times $T_1$, $T_2^*$, and/or $T_2$ as a function of position, and/or to estimate one, two, or other multi-dimensional distributions of $T_1$ versus $T_2^*$, or other relaxation time combinations, as a function of position.

Some example surface NMR measurement apparatus may include, inter alia, surface NMR measurement hardware such as a computer/controller, data acquisition devices, a voltage/current generator, transmit switching, signal receive electronics, and/or detection coils. The computer or other controller may be configured with surface NMR measurement control circuits or software configured to execute the surface NMR measurement techniques disclosed herein. Some example NMR measurement data processing apparatus may include a computer configured with NMR data processing software configured to process NMR data gathered according to the disclosed surface NMR measurement techniques to estimate relaxation times $T_1$, $T_2^*$, and/or $T_2$ as a function of position, and/or to estimate one-dimensional, two-dimensional or other multi-dimensional distributions of relaxation times as a function of position as described herein.

Further aspects and variations are discussed in detail below.

BRIEF DESCRIPTION OF THE DRAWINGS

Various features and attendant advantages of the disclosed technologies will become fully appreciated when considered in conjunction with the accompanying drawings, in which like reference characters designate the same or similar parts throughout the several views, and wherein:

FIG. 4A, FIG. 4B, and FIG. 4C illustrate three example types of preparatory pulses: on-resonance, composite, and adiabatic.

FIG. 10A, FIG. 10B, and FIG. 10C are graphs illustrating example excitation as a function of position beneath a surface NMR coil for one on-resonance pulse and two adiabatic pulses.

DETAILED DESCRIPTION

Figure 1:
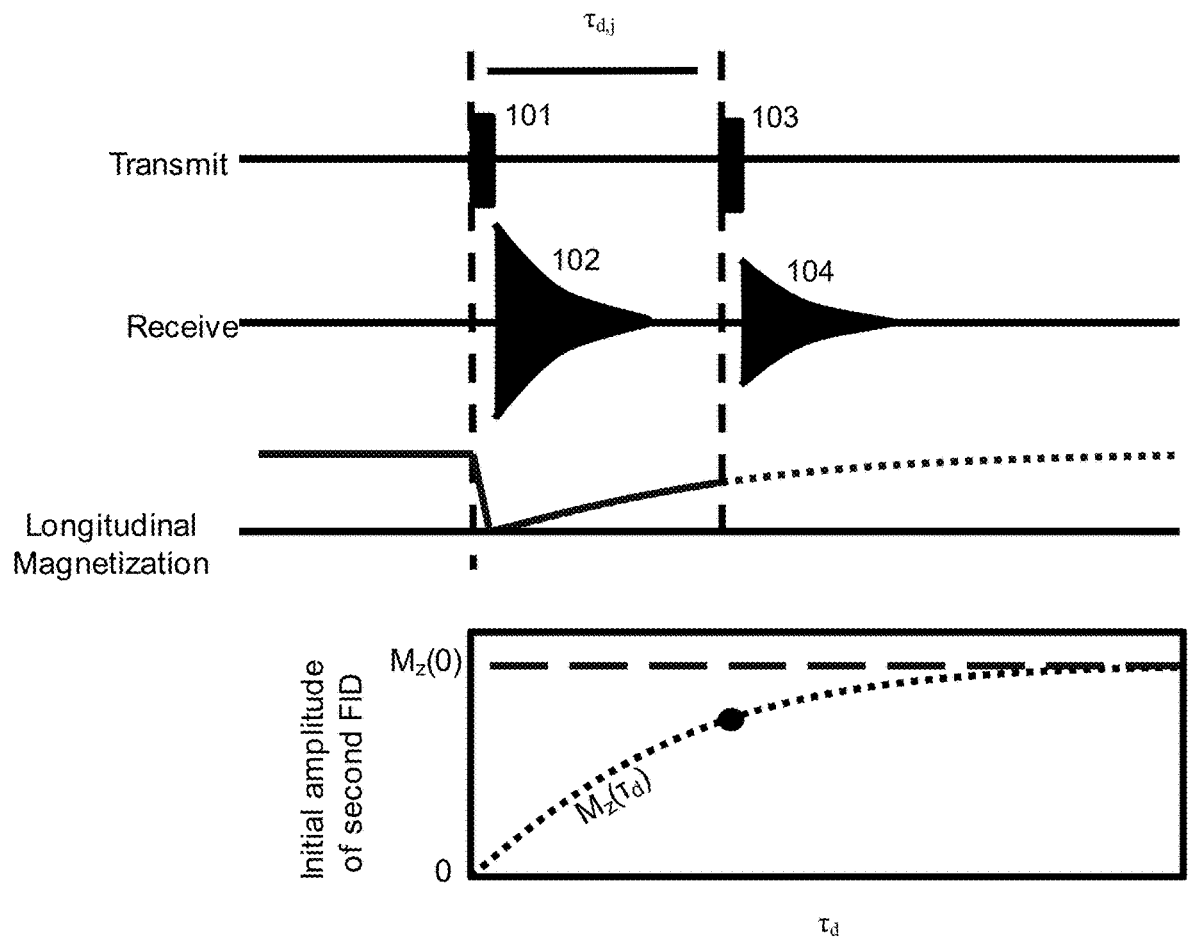
FIG. 1 illustrates an example acquisition sequence for a laboratory saturation recovery experiment.

Prior to explaining embodiments of the invention in detail, it is to be understood that the invention is not limited to the details of construction or arrangements of the components and method steps set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

Technologies directed to NMR relaxation time estimation are disclosed. The attached figures illustrate, inter alia: surface NMR acquisition methods; techniques to estimate NMR relaxation times; and surface NMR apparatus. Example surface NMR acquisition methods may include generating a set of two or more multi-pulse acquisition sequences, each of the multi-pulse acquisition sequences comprising an initial preparatory pulse followed by one or more subsequent "depth sensitive" pulses. The preparatory pulses may have substantially identical properties across the set of multi-pulse acquisition sequences, while the pulse moments of the depth sensitive pulses may be varied in the set of multiple acquisition sequences. The term "substantially identical" in the context of preparatory pulses having substantially identical properties, refers to having a difference equal to or less than 5% of the larger preparatory pulse. For example, on-resonance preparatory pulses with pulse moments of 10 Amp seconds (As) and 10.5 As would be considered "substantially identical" for the purpose of this disclosure.

Example techniques to estimate NMR relaxation times may include processing techniques for processing NMR data acquired with disclosed surface NMR acquisition methods. Acquired NMR data may be used to estimate NMR properties and relaxation times such as $T_1$ and $T_2^*$ as a function of position as well as one-dimensional and two-dimensional covariance distributions of relaxation times as a function of position. Resulting estimates of the relaxation time properties of the subsurface and their spatial distribution can be used to estimate other properties of the subsurface, including pore size and permeability.

Example surface NMR apparatus may include hardware, control software and/or processing software to execute surface NMR acquisition sequences and/or NMR data processing tasks. Surface NMR apparatus may be configured to generate pulse sequences with pulse types, pulse moments, amplitudes, time delays, relative phases, or other pulse properties according to the surface NMR techniques disclosed herein. NMR data processing apparatus may be configured to use recorded NMR signals in techniques to estimate NMR relaxation times introduced above, namely, to estimate NMR properties and relaxation times as a function of position as well as one-dimensional and two-dimensional covariance distributions of relaxation times as a function of position. NMR data processing apparatus may also be configured to use resulting estimates of relaxation times of the subsurface and their spatial distribution to estimate other properties of the subsurface including pore size and permeability.

The present disclosure appreciates that not all decay times provide equivalent sensitivity to pore size and permeability. In particular $T_2^*$, which is often the most straightforward parameter to measure, is often more sensitive to inhomogeneity in the background magnetic field than to pore size or permeability. The relaxation time $T_2$ can also be significantly affected by magnetic inhomogeneity. The relaxation time which is generally least sensitive to magnetic field inhomogeneity and is most sensitive to pore size and permeability is $T_1$; however, $T_1$ is generally a more challenging relaxation time to measure by surface NMR.

In some embodiments, methods according to this disclosure may constrain the mathematical estimation of $T_1$ to yield more accurate values of the $T_1$ relaxation time. Methods according to this disclosure may incorporate information pertaining to the covariance of $T_1$ with other relaxation times, which can be used to improve the precision and interpretation of relaxation time estimates.

FIG. 1 illustrates an example acquisition sequence for a laboratory saturation recovery experiment. The sequence illustrated in FIG. 1 comprises two transmit operations 101 and 103, shown on the "transmit" line, wherein transmit operation 101 is followed by a receive operation 102, and transmit operation 103 is followed by a receive operation 104, shown on the "receive" line. The transmit pulses 101 and 103 are separated by a delay time referred to as $\tau_{d,j}$. A longitudinal magnetization of a sample to which transmitted pulses are applied is illustrated underneath the receive line. FIG. 1 furthermore includes an example saturation recovery curve can be generated by repeating the illustrated sequence of transmit and receive operations while varying the delay times $\tau_{d,j}$ between each jth pulse sequence.

In a laboratory NMR measurement, the characterization of decay times for a sample volume may be generally straightforward, providing for high precision and accuracy. An example laboratory NMR measurement begins by placing a sample of known volume containing a hydrogen-bearing fluid in a static magnetic field. At equilibrium with the static magnetic field, the hydrogen nuclei produce a net nuclear spin magnetization that is aligned parallel to the direction of the background magnetic field (along the "longitudinal" or z axis).

A coil or antennae may then be used to apply an oscillating magnetic field transmit pulse to the sample, for example in the first transmit operation 101. The applied oscillating magnetic field is referred to as $B_1$ and in the case of an on-resonance pulse may be tuned to the Larmor frequency of the hydrogen nuclei, referred to as $f_0$. The application of $B_1$ causes the spins to rotate an angle $\alpha$, which is proportional to the pulse moment q of the transmit operation. For an on-resonance pulse transmitted at frequency $f_0$, q is given by the product of the $B_1$ field amplitude within the sample and the duration of the $B_1$ magnetic field produced by the transmit pulse.

After the transmit pulse 101 is extinguished, the component of the magnetization in the sample that was rotated into the so-called "transverse plane" (perpendicular to the longitudinal axis), processes about the longitudinal axis generating a detectable NMR signal that resonates at the Larmor frequency. The NMR signal may be detected and observed in the first receive operation 102. The NMR signal following a transmit pulse is referred to as the Free-Induction Decay (FID) signal. The FID signal decays over time as magnetization in the transverse plane simultaneously loses coherence and recovers to equilibrium alignment along the longitudinal axis.

The effective transverse relaxation time $T_2^*$ describes the characteristic decay time of coherent magnetization in the transverse plan and can be observed directly as the decay time of the FID signal. The transverse relaxation time $T_2$ describes the characteristic decay time of coherence magnetization in the transverse plane with elimination or mitigation of static de-phasing in an inhomogeneous field. The longitudinal relaxation time $T_1$ describes the characteristic time required for the magnetization to recover to equilibrium along the longitudinal axis. Because the state of the longitudinal magnetization is not directly indicated by the decay FID signal, a multi-pulse measurement sequence may be used to quantify $T_1$.

The so-called "saturation recovery" method is illustrated in FIG. 1. The "saturation recovery" method starts with the system at equilibrium, with magnetization of a sample aligned along the longitudinal axis ($M_z=M_0$) prior to the application of an initial "saturation" pulse, e.g., the first transmit operation 101 illustrated in FIG. 1. In the laboratory, the value of q for the saturation pulse may be set such that the $B_1$ magnetic field produced by the saturation pulse induces a $\alpha=90$ degree flip of the magnetization across the entire sample volume; thus magnetization of the sample is rotated into the transverse plane, and there remains substantially zero longitudinal magnetization immediately after the saturation pulse ($M_z=0$).

Following the saturation pulse, an FID signal may be observed at the first receive operation 102, and the longitudinal magnetization of the sample may begin to recover along the longitudinal axis with characteristic recovery time specified as $T_1$.

After a finite delay time $\tau_d$, a subsequent 90 degree pulse may be applied, e.g., the transmit operation 103. This subsequent pulse acts to rotate the magnetization of the sample which has recovered along the longitudinal axis back into the transverse plane. A subsequent FID signal may be observed in a subsequent receive operation 104. The observed magnitude of the subsequent FID signal may substantially exactly reflect the magnitude of the longitudinal magnetization $M_z(\tau_d)$ that had recovered to equilibrium prior to application of the subsequent pulse.

By repeating this sequence using a range of delay times, and recording the values of $M_z(\tau_d)$, a saturation recovery curve can be generated that reflects the recovery of the longitudinal magnetization as a function of delay time. For example the sequence may be repeated M times where the value of the delay time $\tau_{d,j}$ is varied in each jth-indexed sequence. An example saturation recovery curve is illustrated at the bottom of FIG. 1. Fitting the curve with an exponential or multi-exponential function (e.g., by Laplace inversion) may provide an estimate of the $T_1$ relaxation time or $T_1$ relaxation time distribution. While methods such as illustrated in FIG. 1 may work in the laboratory, the real-world circumstances of surface NMR measurement in the field makes it more difficult to estimate relaxation times, and in particular to estimate $T_1$, outside the laboratory.

Figure 2:
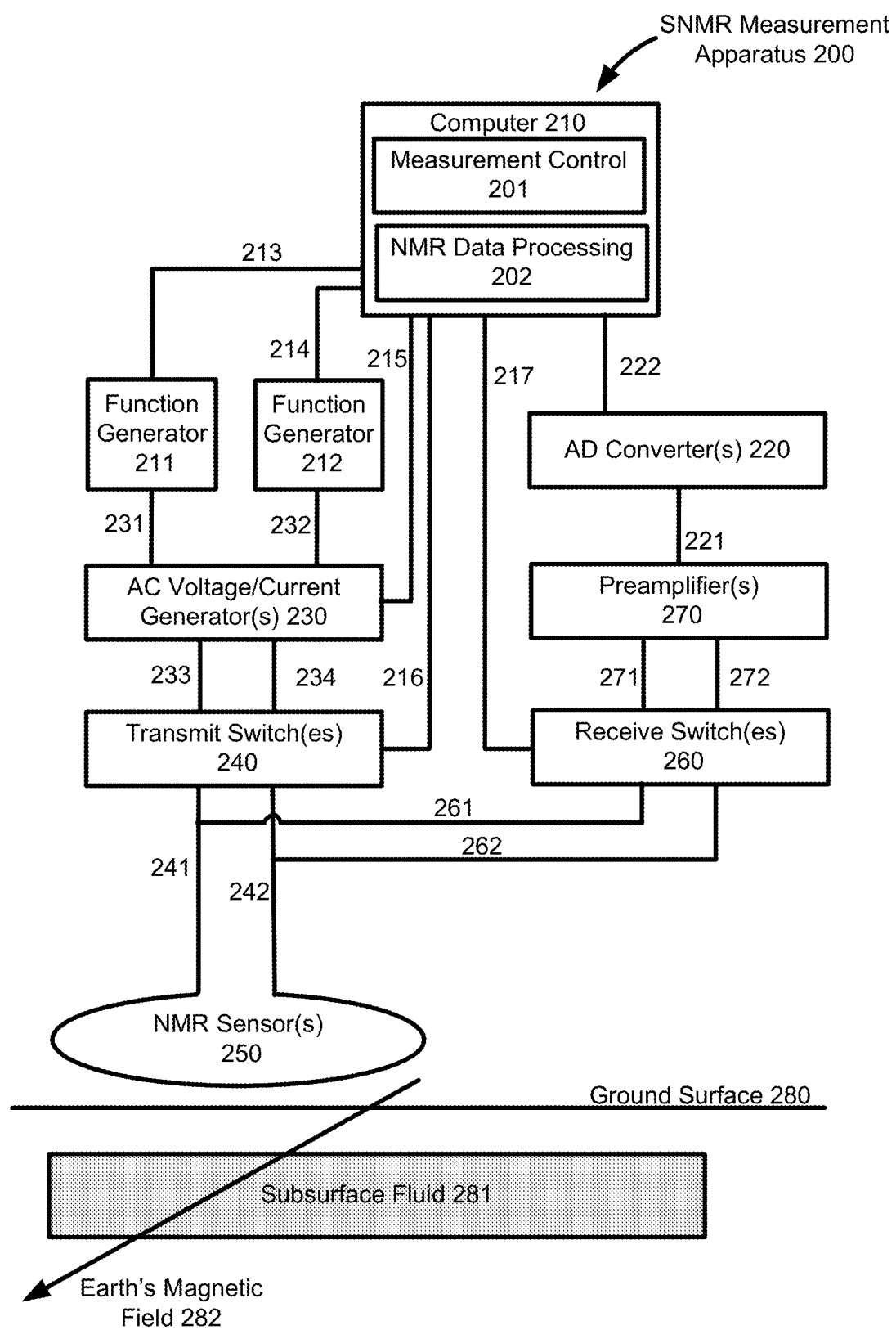
FIG. 2 is a block diagram illustrating an example surface NMR measurement apparatus.

FIG. 2 depicts an example surface NMR measurement apparatus according to this disclosure. The example surface NMR measurement apparatus 200 may include a computer 210, function generators 211, 212, AC voltage/current generator(s) 230, transmit switch(es) 240, NMR sensor(s) 250, receive switch(es) 260, preamplifier(s) 270, and Analog to Digital (AD) converter(s) 220. The NMR sensor(s) 250 are illustrated as an induction coil. Computer 210 comprises measurement control module(s) 201 and data processing module(s) 202. The NMR sensor(s) 250 may be positioned over a ground surface 280, and a subsurface fluid 281 is shown under the ground surface 280. An arrow representing an example direction of Earth's magnetic field 282 is also shown.

In FIG. 2, the computer 210 may be coupled to function generators 211, 212 by connections 213 and 214, respectively. The computer 210 may also be coupled to AC voltage/current generator(s) 230 by connection 215, to transmit switch(es) 240 by connection 216, to receive switch(es) 260 by connection 217, and to AD converter(s) 220 by connection 222. Furthermore, function generators 211, 212 may be coupled to AC voltage/current generator(s) 230 by connections 231 and 232, respectively. AC voltage/current generator(s) 230 may be coupled to transmit switch(es) 240 by connections 233 and 234. Transmit switch(es) 240 may be coupled to both ends 241 and 242 of the induction coil implementing NMR sensor(s) 250. The ends of the induction coil(s) 241 and 242 may be coupled to receive switch(es) 260 by connections 261 and 262, respectively. Receive switch(es) 260 may be coupled to preamplifier(s) 270 by connections 271 and 272. Preamplifier(s) 270 may be coupled to AD converter(s) 220 by connection 221.

In general, with regard to FIG. 2, measurement control module(s) 201 may be configured to perform NMR measurements according to this disclosure by appropriately controlling the various other illustrated components of the surface NMR measurement apparatus 200. For example, the various components may be operated to produce current pulses on the NMR sensor(s) 250, to thereby create NMR excitation pulses. Properties of transmitted pulses, delay times between pulses, and any other aspects of pulse sequences may be adjusted to produce sets of multi-pulse acquisition sequences according to this disclosure. The computer 210 may be configured to produce a pulse by selecting a pulse phase, pulse moment, and/or other pulse properties, and activating the AC voltage/current generator(s) 230. The computer 210 may also be configured to establish appropriate delay times between pulses in multi-pulse acquisition sequences. The computer 210 may be configured to select a pulse phase for example by activating a function generator 211 or 212 corresponding to a desired pulse phase, so that the selected function generator 211 or 212 provides an input pulse phase to the AC voltage/current generator(s) 230, which may then be amplified by the AC voltage/current generator(s) 230 to produce a corresponding pulse on the NMR Sensor(s) 250. The computer 210 may also optionally be configured to close one or more transmit switch(es) 240 when activating the AC voltage/current generator(s) 230, and open the transmit switch(es) 240 after activating the AC voltage/current generator(s) 230.

Surface NMR measurement apparatus 200 may also be configured to receive and record NMR signal data received via the NMR sensor(s) 250. Surface NMR measurement apparatus 200 may be configured to receive and record NMR signal data after one or more excitation pulses. In some embodiments, the computer 210 may be configured to close the receive switch(es) 260 after a pulse. The preamplifier(s) 270 amplify NMR signals received via induction coil(s) 250. The AD converter(s) 220 convert the received and amplified signals to digital NMR signal data, e.g. by sampling received NMR signals at a desired sampling rate, and the computer 210 or other device equipped with storage media may be configured to store the resulting digital NMR signal data.

In some embodiments, the NMR data processing module 202 may be configured to process NMR measurement data, generated by operation of the measurement control module 201 and the various other components of surface NMR measurement apparatus 200. NMR data processing module 202 may be configured to estimate NMR relaxation times as disclosed herein, e.g. as described in connection with FIG. 7 and FIG. 8. It will be appreciated that while the computer 210 may be configured to include NMR data processing module 202, in some embodiments NMR measurements and NMR data processing may be performed separately, e.g., by first performing measurements with system 200, then processing acquired NMR data at a later time and/or with a different computing device comprising NMR data processing module 202, or by a human operator.

It will be appreciated that surface NMR measurement apparatus may be configured differently than illustrated in FIG. 2 in some embodiments. To recite just a few of the many possible configuration options, computer 210 may be programmed with software that controls the generation of pulse sequences and the acquisition of NMR data. A set of data acquisition devices may comprise devices configured generate the control signals for the pulse sequences, such as function generators 211, 212, and AD converter(s) 220 that receive, convert and/or record NMR signals. The AC voltage/current generator(s) 230 may be configured to generate one or more current pulses in the induction coil(s) 250 in a transmit mode, to induce a coherent precession of NMR spins in a sample volume. Optional transmit switch(es) 240 may be configured to isolate transmitter noise from the receive circuitry during a receive mode. NMR sensor(s) 250 may be arranged other than as induction coils, and may be configured in a variety of ways as described herein or as known or as may be developed in the art. Optional receive switch(es) 260 may be configured to isolate the receive preamplifier(s) 270 from the potentially large voltage on the NMR sensor(s) 250 during transmit mode. Optional preamplifier(s) 270 may be configured to amplify the detected NMR signals prior to digitization by the AD converter(s) 220. The optional transmit switch(es) 240 and receive switch(es) 260 may comprise active devices such as relays, and/or passive devices such as diodes. Optional tuning capacitors, not shown in FIG. 2, may be used in the transmit mode to increase the transmitted current in the induction coil(s) 250, and/or in receive mode to increase the amplitude of the NMR signal voltage across the terminals of the induction coil(s) 250.

In some embodiments, NMR sensor(s) 250 may comprise an array of coils comprising one or more transmit coils, one or more receive coils, and/or one or more combination transmit and receive coils. For example, NMR sensor(s) 250 may comprise one transmit coil and multiple receive coils. NMR sensor(s) 250 may comprise one combination transmit and receive coil, and multiple receive coils. NMR sensor(s) 250 may comprise multiple combination transmit and receive coils. These and other multicoil arrangements may be configured in some embodiments as will be appreciated. Multicoil arrangements may be useful for localization of fluids in structure 280, as described for example in U.S. Pat. No. 2,466,128, entitled "Multicoil Data Acquisition and Processing Methods," issued Dec. 16, 2008, which is incorporated by reference herein.

Any combination of hardware and software that enables the acquisition and processing of NMR signals is suitable to implement embodiments of this disclosure. An architecture to implement the disclosed methods could comprise, for example, elements illustrated in FIG. 2, such as an AC voltage and current generator 230, a digital control system implemented at least in part by computer 210, a transmit switching circuit including transmit switch(es) 240, a receive switching circuit including receive switch(es) 260, a multi-channel receive circuit including, e.g., a plurality of induction coils in NMR sensor(s) 250, preamplifier(s) 270, a digital acquisition system including AD converter(s) 220, a digital storage device which may be implemented within computer 210 or other digital storage device, and a digital computer 210. The switching circuits may transition a system such as 200 between a transmit-mode, when the coil(s) 250 are connected to the transmit circuit, and receive-mode when the coil(s) 250 are connected to the receive circuit.

In general, NMR measurements may be collected by transmitting one or more pulses of alternating current through NMR sensor(s) 250. The alternating current may be tuned to the Larmor frequency of hydrogen nuclei, for example, and may generate a magnetic field in a subsurface fluid 281 alternating at the Larmor frequency. The alternating magnetic field radiates into the subsurface fluid 281 and modifies the nuclear magnetization state of hydrogen atoms present in subsurface fluid 281. The transmitted alternating magnetic field perturbs the magnetization from equilibrium alignment in a static magnetic field, so that some component of the nuclear magnetization rotates into the transverse "xy" plane. Once rotated from equilibrium, the magnetization relaxes over time back to the equilibrium state over time, decaying from the transverse plane and re-growing along the longitudinal axis. The rotation of the magnetization by the transmitted pulse(s) and subsequent relaxation to equilibrium are described by the phenomenological Bloch equations. The evolution of the magnetization under the Bloch equations depends on several variables including the amplitude of the transmitted field, the duration and timing of the transmitted field, the phase of the transmitted field, the longitudinal relaxation time $T_1$, FID relaxation rate $T_2^*$, and/or the spin-spin relaxation time T2 of the hydrogen nuclei under investigation. These aspects of NMR measurement may be used in determining the various NMR properties described herein.

In surface NMR measurement of subsurface fluids, the Earth's magnetic field 282 may be utilized as the static background field and the $B_1$ field may be generated by transmitting current through one or more wire loops 250 laid out on the ground surface. Commonly an on-resonance excitation pulse is used (i.e., transmitted at the Larmor frequency $f_0$) The resulting excitation and precession of the nuclear magnetization in subsurface fluids 281 induces a voltage on the same coil 250 or additional coils, and the coil voltage may be recorded at computer 210 as the received NMR signal.

In contrast to laboratory measurements, for which the $B_1$ field is uniform over the investigated volume, for surface NMR measurements in the field the $B_1$ magnetic field varies over the subsurface volume (i.e. the $B_1$ magnetic field is always stronger closer to the coil). As a result, there may be a distribution of the $B_1$ magnetic field amplitude and thus, for an on-resonance pulse, a distribution of tip angles within the subsurface following the transmitted pulse. Fluids located at a particular position in the subsurface exhibit a maximum amplitude response if the tip angle at that position is close to 90 degrees or 270 degrees and a minimum amplitude response if the tip angle at that position is close to 0 degrees or 180 degrees. By increasing or decreasing the product q of current I on the coil 250 during the transmitting pulse and the transmitting pulse duration $t_p$, the distribution of tip angles α as a function of subsurface position may be varied as well as the sensitivity of the measurement to fluids at varying depths. The product q may be referred to as the pulse moment. The maximum excitation depth is a function of q: as the pulse moment is increased, the maximum excitation depth is also increased. We use the term "maximum excitation depth" of a pulse to refer to the depth below which tip angle rotations resulting from the pulse are substantially less than 30 degrees, e.g., anywhere from 0 degrees to 15 degrees. It will be appreciated that any tip angle may be selected for the purpose of measuring maximum excitation depth. A mathematical inversion of the recorded data measured for different values of q may be used to estimate the variation in NMR parameters as a function of depth.

In an example single-pulse NMR FID measurement scheme, a single acquisition sequence may comprise transmitting one on-resonance pulse with finite duration $t_p$ and a current I on a surface loop and then recording the subsequent NMR FID signal as one or more voltage measurements. A complete data set may comprise a collection of N single acquisition sequences, where the value of q is varied between each ith acquisition sequence. The magnitude of I may be varied, and the duration of the pulse, $t_p$, may also be varied to vary q. Identical single acquisition sequences may be repeated to increase the signal-to-noise ratio.

The NMR voltage V(t,q) measured in the coil as a function of time and q can be expressed in a forward model as the product of the spatial distribution of water content and $T_2^*$ decay behavior at each subsurface location r, and a kernel K(r,q) that represents underlying NMR physics, parameters of the coil geometry, parameters of the transmitted pulse, and other known parameters. A mathematical spatial inversion of the data collected by such a single-pulse scheme, using the aforementioned model, yields the estimated NMR response from each subsurface volume element, reflecting the total longitudinal magnetization existing prior to the pulse (proportional to water content) and the $T_2^*$ decay behavior of the fluid associated with this longitudinal magnetization. The resulting estimates of water content and $T_2^*$ decay behavior as a function of subsurface position can be used to estimate other properties of the subsurface formation, including pore size and permeability. However, the FID relaxation time $T_2^*$ may be less sensitive to pore size and permeability than the relaxation time $T_1$.

Figure 3:
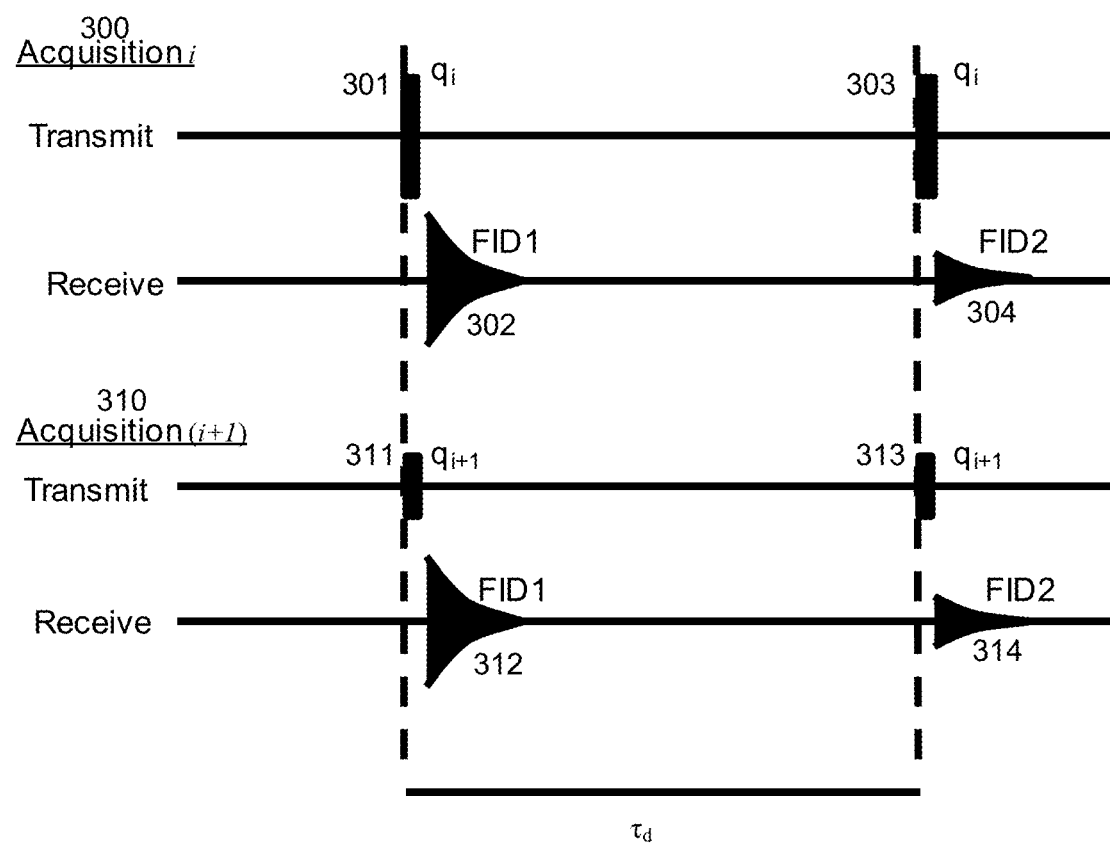
FIG. 3 illustrates an example surface NMR acquisition sequence for a surface NMR "Pseudo Saturation Recovery".

FIG. 3 illustrates an example NMR acquisition sequence for NMR Pseudo Saturation Recovery (PSR). PSR may provide an approach to measuring $T_1$ by NMR which attempts to reproduce the saturation recovery experiment, described above for the case of laboratory conditions. FIG. 3 illustrates a set of multi-pulse acquisition sequences including acquisition i 300 and acquisition i+1 310. Acquisition i 300 may be performed first, and acquisition i+1 310 may be performed next. Each acquisition sequence comprises transmit operations illustrated on a transmit line and receive operations illustrated on a receive line.

In acquisition i 300, a transmit operation 301 is followed by a receive operation 302, there is a delay time $\tau_d$ between transmit operations, and a subsequent transmit operation 303 is followed by a subsequent receive operation 304. Transmit operations 301 and 303 have a pulse moment $q_i$.

In acquisition i+1 310, transmit operation 311 is followed by receive operation 312, there is a delay time $\tau_d$ between the transmit operations, and a subsequent transmit operation 313 is followed by a subsequent receive operation 314. Transmit operations 311 and 313 have a pulse moment $q_{i+1}$. FID signals FID1 are received in receive operations 302 and 312, and FID signals FID2 are received in receive operations 304 and 314. FID1 and FID2 may be different in the different receive operations 302, 312, 304, and 314.

In a basic PSR measurement scheme, a single acquisition sequence may comprise transmitting two on-resonance transmit pulses, such as 301 and 303, separated by an adjustable delay time $\tau_d$. In each single acquisition, the two transmit pulses may have substantially the same q-value. The FID signal following the subsequent transmit pulse ("FID2") may be recorded; the FID following the first pulse ("FID1") may also be recorded. An individual delay time data set may comprise of N single acquisition sequences wherein the value of q for the two transmit pulses is varied between each ith acquisition in the set and the value of $\tau_d$ remains fixed. A complete PSR dataset may comprise M multiple individual delay time datasets between which the value of $\tau_d$ is varied between each jth-indexed acquisition.

While the PSR dataset V(t, q, $\tau_d$) may be sensitive to the $T_1$ recovery, the PSR dataset V(t, q, $\tau_d$) may be inadequate to quantify the spatial variation in $T_1$ behavior in the subsurface. This is in part because the kernel that describes the PSR voltage signal in a forward model is a function of $T_1$; thus, the mathematical inversion is non-linear and poorly conditioned. In light of this complication, the following simplifying assumptions might be made: (i) within the subsurface volume contributing to the signal, the preparatory pulse is assumed to produce substantially a 90 degree tip angle and zero longitudinal magnetization; (ii) the signal following the subsequent pulse only reflects the magnitude of the longitudinal magnetization the recovers during the delay time. As such, the PSR experiment may be approximated as an ideal saturation recovery experiment. However, this approach may have limited validity and certain drawbacks described below.

In fact, the above listed simplifying assumptions are generally at least partially invalid for the PSR dataset because both on-resonance pulses in each double-pulse sequence actually produce a range of tip angles within the subsurface. For volumes in which the tip angle is far from 90 degrees, a residual portion of the magnetization will be left along the longitudinal axis following the first pulses, and the longitudinal component will be non-zero. This residual magnetization will be excited by the subsequent pulses into the transverse plane; thus, such volumes where the tip angle is far from 90 degrees will contribute to the signal following the subsequent pulses that is associated with magnetization that has undergone $T_1$ recovery. As a result, the use and interpretation of PSR data can lead to errors in estimated values of $T_1$.

In addition to a need for improved determinations of $T_1$, NMR measurements may be improved by methodology for utilizing sensitivity of the measurement to the covariance of the $T_1$ and $T_2^*$ relaxation times in a geologic formation. Covariance of different NMR relaxation times can be exploited to improve the characterization of subsurface formations. For example, dense sampling of one relaxation time can be used to improve the resolution of a subsequent relaxation time. Further, the two-dimensional relaxation time distribution derived from a two-dimensional inversion of relaxation times can provide more detailed information about the properties of the subsurface formation and fluid contained therein. For surface NMR, $T_1$ and $T_2^*$ may show significant covariance and this covariance may be exploited to provide additional constraint for the data inversion and more detailed characterization of the geologic formation. Thus in some embodiments, methodologies may use theoretically bounded covariance of $T_1$ and $T_2^*$ to constrain and provide improved estimation of relaxation time magnitudes. For example, it is known that $T_2^*$ is never longer than $T_1$, and this may be used (among other theoretically established covariance properties) to constrain estimation of $T_1$. In some embodiments, estimated covariance of $T_1$ and $T_2^*$ can be used to provide more detailed characterization of a geological formation than $T_1$ or $T_2^*$ alone.

The methods described in connection with FIG. 1 and FIG. 3 use on-resonance pulses and do not take advantage other pulse types or pulse sequence properties, described below, that may be useful for surface NMR measurements. Other pulse types and pulse sequences included in the present disclosure are illustrated in FIGS. 4A, 4B, and 4C, FIGS. 5A, 5B, and 5C, and FIG. 6.

FIG. 4A illustrates properties of an on-resonance pulse. FIG. 4B illustrates properties of a composite pulse. FIG. 4C illustrates properties of an adiabatic pulse. In an on-resonance pulse as illustrated in FIG. 4A, the current amplitude $I(t)$, phase $\varphi(t)$, and frequency $f(t)$, may be held constant over the duration of the pulse. In a composite pulse as illustrated in FIG. 4B, the phase and/or the amplitude of the pulse may be changed between two or more discrete intervals of the pulse, e.g., from a value of $I_0$ to a value of $I_i$ and from a value of $\varphi_0$ to a value of $\varphi_1$. In an adiabatic pulse as illustrated in FIG. 4C, the amplitude of the pulse and/or the frequency of the pulse may be varied continuously over the duration of the pulse. For example, $I(t)$ may be varied from 0 to a maximum value of $I_{max}$ as the frequency is varied from an off-resonance value of $f_{off}$ to the on-resonance Larmor frequency $f_0$.

By selecting appropriate functions for $I(t)$, $\varphi(t)$, and $f(t)$, composite and adiabatic pulses can produce tip angles in subsurface volumes underneath NMR surface coils that may be substantially uniform over a wider range of $B_1$ field strength, and thus may be substantially more uniform over a wider range of distances from the surface coil, than may be achieved using standard on-resonance pulses. For example, composite and adiabatic pulses can be designed to produce tip angles that are close to 90 degrees over a wide range of depths (e.g. adiabatic half-passage) or 180 degrees over a wide range of depths (e.g. adiabatic full-passage).

While on-resonance pulses may be distinguished from other on-resonance pulses by differences in pulse moment, composite and adiabatic pulses do not have a single pulse moment value. That said, "effective" pulse moment values may be calculated to distinguish composite pulses from other composite pulses, and adiabatic pulses from other adiabatic pulses. Another way to distinguish on-resonance, composite, and adiabatic pulses is by maximum excitation depth. The maximum excitation depth of an on-resonance pulse, a composite pulse or an adiabatic pulse is generally a function of $I(t)$, $\varphi(t)$, and $f(t)$ for the pulse. The maximum excitation depth of a composite pulse or an adiabatic pulse is also generally less than the maximum excitation depth of an on-resonance pulse with an equivalent value of $\int I(t)dt$. This disclosure may therefore refer to differences in maximum excitation depth or to differences in pulse moment to distinguish between pulses in some circumstances.

Improved Pulse Sequences

Figure 5A:
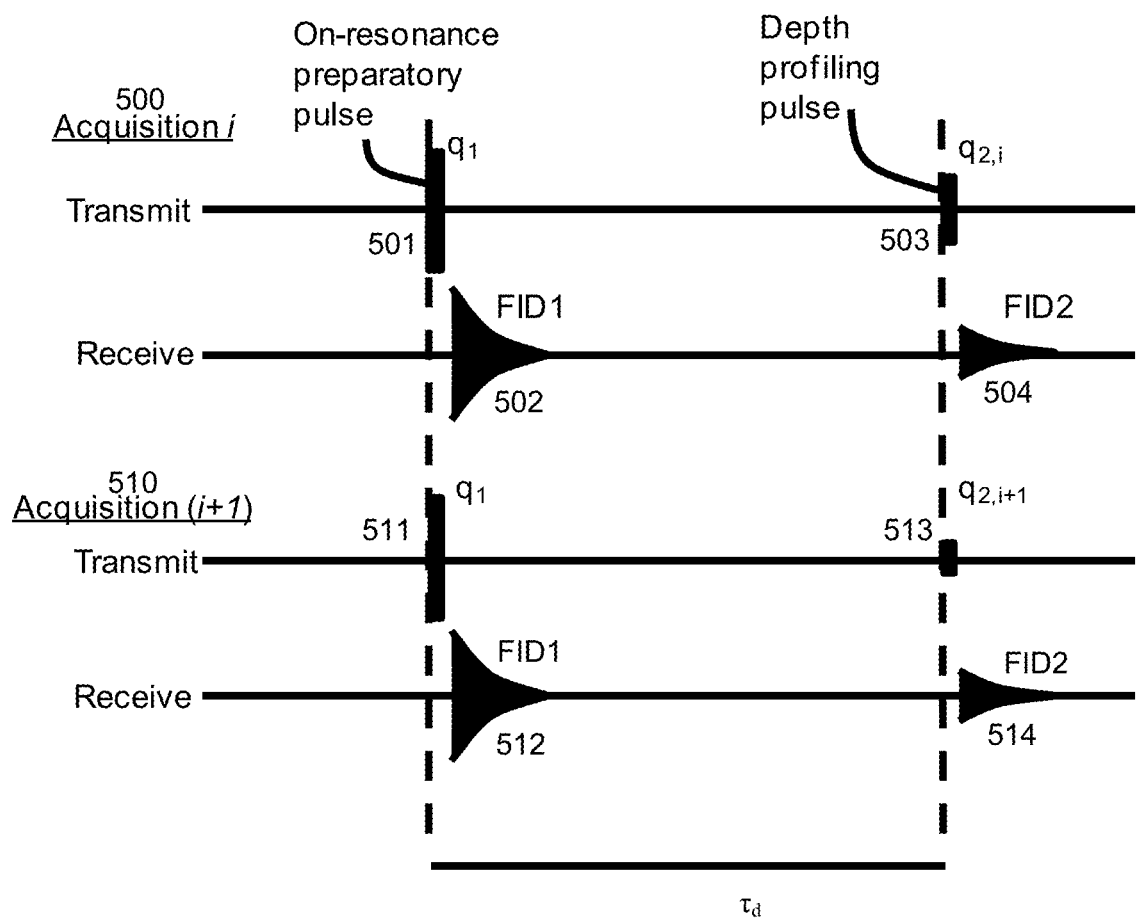
FIG. 5A, FIG. 5B, and FIG. 5C illustrate example surface NMR acquisitions in "crush recovery" sequences.
Figure 5B:
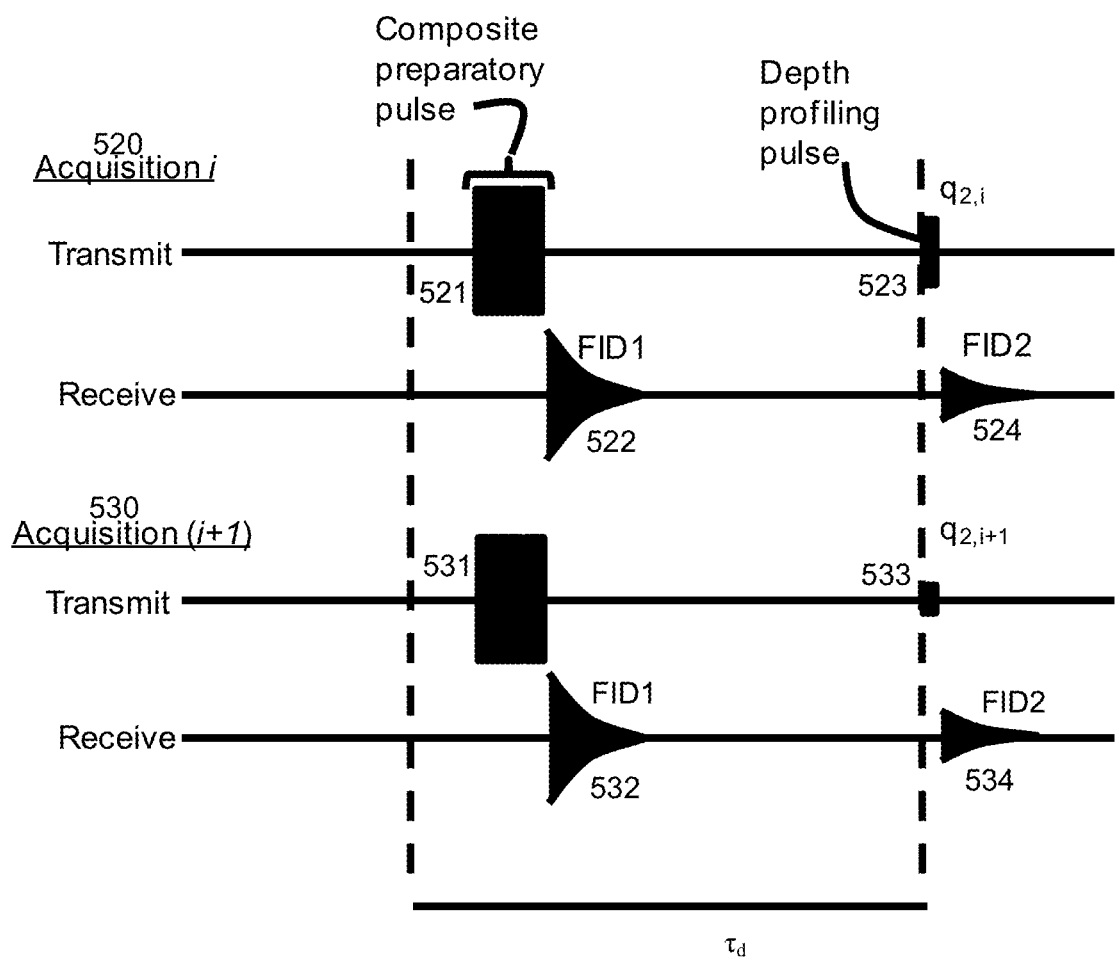
Figure 5C:
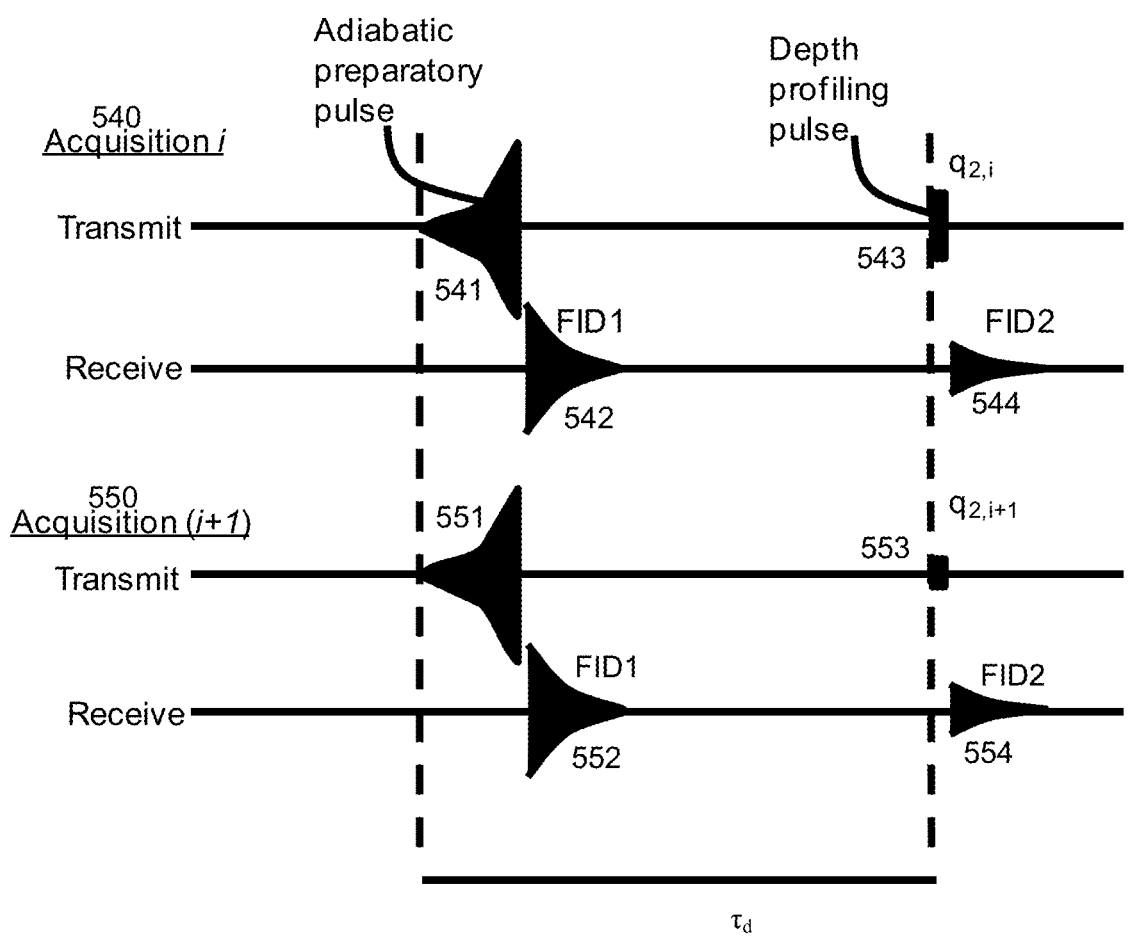

FIGS. 5A, 5B, and 5C illustrate example surface NMR acquisitions in "crush recovery" sequences. FIGS. 5A, 5B, and 5C illustrate a class of acquisition sequences, which differ from the PSR acquisition sequence shown in FIG. 3. Unlike the PSR sequence for which the preparatory pulse changes between each ith acquisition, for the sequences shown in FIGS. 5A, 5B, and 5C, the initial "preparatory" pulse may be substantially identical between each ith acquisition, and the second or other subsequent "depth profiling" pulse may be changed between each ith acquisition. Thus, the maximum excitation depth of the preparatory pulse may be substantially identical for the set of N measurements with varied $q_2$.

FIG. 5A illustrates a NMR acquisition comprising a set of two multi-pulse acquisition sequences for simplicity of explanation, understanding that sets may comprise any number of multi-pulse acquisition sequences. The multi-pulse acquisition sequences are referred to as acquisition i 500 and Acquisition i+1 510. Each sequence comprises transmit operations and receive operations.

During a transmit operation 501 of acquisition i 500, an on-resonance preparatory pulse with pulse moment $q_1$ is transmitted. The transmit operation 501 is followed by a receive operation 502 in which NMR signals FID1 are received. During a subsequent transmit operation 503 of acquisition i 500, an on-resonance depth profiling pulse with pulse moment $q_{2,i}$ is transmitted. The subsequent transmit operation 503 is followed by a subsequent receive operation 504 in which NMR signals FID2 are received.

Acquisition i+1 510 may be performed after acquisition i 500. As with acquisition i, during a transmit operation 511 of acquisition i+1 510, an on-resonance preparatory pulse with pulse moment $q_1$ may be transmitted. The transmit operation 511 may be followed by a receive operation 512 in which NMR signals FID1 are received. During a subsequent transmit operation 513 of acquisition i+1 510, an on-resonance depth profiling pulse with pulse moment $q_{2,i+1}$ is transmitted. The subsequent transmit operation 513 may be followed by a subsequent receive operation 514 in which NMR signals FID2 are received.

In FIG. 5A, the pulse moment $q_1$ of the on-resonance preparatory pulses 501 and 511 (or the maximum excitation depth of the on-resonance preparatory pulses) may be substantially identical in acquisition i 500 and acquisition i+1 510. The pulse moments $q_{2,i}$ and $q_{2,i+1}$ of the depth profiling pulses 503 and 513, however, may be substantially different. While any difference between depth profiling pulses 503 and 513 may be usefully applied depending on the circumstances, some embodiments may comprise differences ranging between 0.5×, in which the largest depth profiling pulse is 50% larger than the smallest depth profiling pulse, and 10,000×, in which the largest depth profiling pulse is 10,000 times larger than the smallest depth profiling pulse. The term "substantially different" in the context of difference between pulse moments of depth profiling pulses refers to any difference equal to or greater than 0.5×, in which the largest depth profiling pulse is 50% larger than the smallest depth profiling pulse. Difference between depth profiling pulses 503 and 513 in the general range of about 500×, in which the largest depth profiling pulse is about 500 times larger than the smallest depth profiling pulse may prove useful in many embodiments. It should be understood that in embodiments comprising many acquisitions, there may be small differences between the depth profiling pulses of some acquisitions and larger differences between the depth profiling pulses of other acquisitions.

Furthermore, in FIG. 5A, the pulse moment $q_1$ of the on-resonance preparatory pulses 501 and 511, and thus the maximum excitation depth of pulses 501 and 511, may be substantively different from the pulse moments $q_{2,i}$ and $q_{2,i+1}$ of the depth profiling pulses 503 and 513. When the pulse moment $q_1$ of preparatory pulses 501 and 511 is substantively greater than the pulse moments $q_{2,i}$ and $q_{2,i+1}$ of the depth profiling pulses 503 and 513, the maximum excitation depth of preparatory pulses 501 and 511 may be greater than the maximum excitation depths of depth profiling pulses 503 and 513.

For the purpose of this disclosure, the term "substantively different" in the context of differences between pulse moments (or maximum excitation depths) of preparatory pulses and pulse moments (or maximum excitation depths) of depth profiling pulses refers to any difference equal to or greater than 25% of the smaller pulse moment or smaller maximum excitation depth. In some embodiments, differences between pulse moments (or maximum excitation depths) of preparatory pulses and pulse moments (or maximum excitation depths) of depth profiling pulses may be equal to or greater than 50% of the smaller pulse moment or smaller maximum excitation depth. It is noted that using a single DC power supply the transmission of a long pulse or long pulse sequence may decrease energy stored on the power supply such that the bus voltage decreases as energy is dissipated in the pulses, and the resulting pulses show a decreased amplitude (and therefore, decreased pulse moment) as the energy is dissipated. Such decreases in pulse moment associated only with pulse transmission and dissipation of power supply energy do not comprise a substantive difference in pulse moment as the term is understood herein.

FIG. 5B illustrates a NMR acquisition in which the initial preparatory pulses are composite pulses, and as in FIG. 5A, described above, the preparatory pulses remain substantially identical between each ith acquisition, while the subsequent (depth profiling) on-resonance pulses may be changed between each ith acquisition. FIG. 5B may generally be understood with reference to FIG. 5A, above. FIG. 5B comprises an acquisition i 520 and an acquisition i+1 530, wherein acquisition i 520 comprises transmit operations 521 and 523 and receive operations 522 and 524, and wherein acquisition i+1 530 comprises transmit operations 531 and 533 and receive operations 532 and 534. In contrast with FIG. 5A, however, preparatory pulses 521 and 531 comprise composite, rather than on-resonance pulses, which affects received NMR signals FID1 and FID2 in each receive operation 522, 524, 532, and 534.

The composite preparatory pulses 521 and 531 may be designed with appropriate values of I(t), φ(t), and f(t) so that the maximum excitation depth of the preparatory pulses 521 and 531 may be greater than or equal to the maximum excitation depth of the subsequent pulses 523 and 533. In some embodiments, the maximum excitation depth of the composite preparatory pulses 521 and 531 may be substantively different from the maximum excitation depths of the depth profiling pulses 523 and 533. Preparatory pulses 521 and 531 may also differ qualitatively from depth profiling pulses 523 and 533 in some embodiments, e.g., when the preparatory pulses 523 and 533 comprise composite pulses (with varied f(t) and I(t)) and the subsequent pulses 523 and 533 comprise resonance pulses ($f(t)=f_0$).

FIG. 5C illustrates a NMR acquisition in which the initial preparatory pulses are adiabatic pulses, and as in FIG. 5A, described above, the preparatory pulses remain substantially identical between each ith acquisition, while the subsequent (depth profiling) on-resonance pulses may be changed between each ith acquisition. FIG. 5C may generally be understood with reference to FIG. 5A, above. FIG. 5C comprises an acquisition i 540 and an acquisition i+1 550, wherein acquisition i 540 comprises transmit operations 541 and 543 and receive operations 542 and 544, and wherein acquisition i+1 550 comprises transmit operations 551 and 553 and receive operations 552 and 554. In contrast with FIG. 5A, however, preparatory pulses 541 and 551 comprise adiabatic, rather than on-resonance pulses, which affects received NMR signals FID1 and FID2 in each receive operation 542, 544, 552, and 554.

The adiabatic preparatory pulses 541 and 551 may be designed with appropriate values of I(t), φ(t), and f(t) so that the maximum excitation depth of the preparatory pulses 541 and 551 may be always greater than or equal to the maximum excitation depths of the subsequent pulses 543 and 553. In some embodiments, the maximum excitation depth of the adiabatic preparatory pulses 541 and 551 may be substantively different from the maximum excitation depths of the depth profiling pulses 543 and 553. Preparatory pulses 541 and 551 may also differ qualitatively from depth profiling pulses 543 and 553 in some embodiments, e.g., when the preparatory pulses 543 and 553 comprise composite pulses (with varied f(t) and I(t)) and the subsequent pulses 543 and 553 comprise on-resonance pulses ($f(t)=f_0$).

In some embodiments, at least one multi-pulse acquisition sequence in a set of multi-pulse acquisition sequences according to FIG. 5A, 5B, or 5C may include a substantive difference between an initial preparatory pulse and a subsequent depth profiling pulse in the sequence. Also, in some embodiments, at least one of, and up to all of, the subsequent depth profiling pulses in an individual multi-pulse acquisition sequence (within a set of multi-pulse acquisition sequences) may comprise a substantive difference between the preparatory and subsequent pulses.

FIG. 5A, 5B, or 5C each illustrate a set of acquisitions comprising two acquisitions, wherein each acquisition comprises two transmit pulses and two receive operations. It will be appreciated that sets may comprise additional acquisitions, and that acquisitions may comprise additional pulses. The illustrated depth profiling subsequent pulses may comprise one or more ordered subsequent pulses following the preparatory pulses, each ordered subsequent pulse having a pulse moment or maximum excitation depth, and wherein a pulse moment or maximum excitation depth of an ordered subsequent pulse in at least one of the acquisition sequences in a set may be substantially different from a pulse moment of the same ordered subsequent pulse in at least one other of the acquisition sequences in the set. For example, if an acquisition comprises three subsequent pulses including a first, a second, and a third ordered subsequent pulse, the first, second or third subsequent pulse may be substantially different from a same ordered first, second or third subsequent pulse in at least one other of the acquisition sequences in the set.

In some embodiments, acquisition schemes disclosed herein may be referred to as "Crush Recovery" (CR) sequences. In a CR acquisition scheme, an individual acquisition sequence may comprise transmitting two pulses separated by an adjustable delay time $\tau_d$. The FID signal following the subsequent pulse ("FID2") may be recorded; the FID following the preparatory pulse ("FID1") may also be recorded. A single delay time CR data set may be comprised of N individual acquisition sequences wherein I(t) and f(t) for the initial preparatory pulses are fixed, the pulse moments $q_2$ for the subsequent pulses are varied between individual acquisitions with index i, and the delay time $\tau_d$ remains fixed. A complete CR dataset may be comprised of M multiple individual delay time datasets of index j between which the value of $\tau_d$ is varied. A complete CR dataset for a particular fixed preparatory pulse may comprise a multitude of FID2 signals recorded as a function of time for varying values of $q_2$ and $\tau_d$. It will be appreciated that apparatus according to FIG. 2 may be configured to gather such data sets, and methods may be performed comprising sequences of pulse transmit and receive operations effective to gather such data sets. Such methods may include, inter alia, the use of on-resonance, composite, or adiabatic preparatory pulses, the use of substantially identical preparatory pulses with different subsequent pulses, and/or subsequent pulses with maximum excitation depths that may be substantively smaller than the maximum excitation depth of the preparatory pulses.

In the preceding CR embodiment, the preparatory pulse may be referred to as the "crush" pulse and the subsequent pulse may be referred to as the "depth-profiling" pulse. A purpose of the crush pulse is to negate, substantially mitigate, or invert signals present in the subsequent FID that are associated with the subsurface longitudinal magnetization state existing prior to application of the crush pulse. A purpose of the depth-profiling pulse is to detect, with sensitivity as a function of depth, the component of the longitudinal that has recovered during the delay time.

In the case of an on-resonance crush pulse, the crush pulse may typically have a substantively higher pulse moment and greater maximum excitation depth than the subsequent pulse. Thus, this preparatory pulse induces large tip angles within the same subsurface volumes where the subsequent depth-profiling pulse induces significant amplitude tip angles. Specifically, within volumes sampled by the subsequent pulse, the crush pulse creates large tip angles that may include multiple complete rotations (i.e. rotations greater than 360 degrees). Thus the orientation of the magnetization immediately after the pulse may show a high degree of spatial variability ranging from 0 to 360 degrees over a small spatial scale. Because the subsurface tip angles produced by the application of the preparatory pulse are poorly correlated spatially within the shallower volumes sampled by the subsequent pulse, the initial longitudinal magnetization is effectively crushed and contributes little coherent energy to the subsequent FID signal excited by the subsequent pulse. As a result, the magnetization state prior to the application of the subsequent pulse primarily reflects the component of the longitudinal magnetization that has been subject to $T_1$ recovery prior to application of the subsequent pulse.

In the case of an adiabatic or composite crush pulse, values of I(t), φ(t), and f(t) may be selected such that the pulse produces tip angle near 90 degrees so as to minimize the longitudinal magnetization over a wider range of depths than an on-resonance pulse. Because the crush pulse has also a greater investigation depth than the on-resonance depth-profiling pulse, the crush pulse minimizes the longitudinal magnetization over the same range of depths where the depth-profiling pulse induces spatially coherent and significant amplitude tip angles. Thus, the initial longitudinal magnetization is effectively crushed and contributes little coherent energy to the subsequent FID signal excited by the subsequent pulse. As a result, the magnetization state prior to the application of the subsequent pulse primarily reflects the component of the longitudinal magnetization that has been subject to $T_1$ recovery prior to application of the subsequent pulse. In other embodiments, values of I(t), φ(t), and f(t) may be selected such that the pulse produces tip angles near 180 degrees so as to invert the longitudinal magnetization over the range of depths where the depth-profile pulse produces spatially coherent and significant amplitude tip angles.

Varying the value of $q_2$ for the subsequent depth-profiling pulse between single acquisitions provides sensitivity to the recovered magnetization as a function of depth and spatial location. Varying the value of $\tau_d$ between single delay time acquisitions provides sensitivity to the $T_1$ recovery process over time. In some embodiments, a complete CR dataset can be acquired for more than one value of $q_1$. In other embodiments, identical acquisitions may be repeated and combined to improve the signal to noise ratio.

To implement the acquisition sequences described herein, NMR measurement methods and apparatus according to this disclosure may arbitrarily and independently control the pulse moment q of transmitted pulses. In some embodiments, the value of q may be varied by changing the duration of two pulses independently (i.e., the value of $q_2$ can be made smaller than the value of $q_1$ by shortening the duration of the subsequent pulse). Changing the duration of the pulse, however, changes the effective bandwidth. Thus, in some embodiments, the value of q may instead be changed by varying the current I(t) passed through the surface coil (i.e., the value of $q_2$ can be made smaller than the value of $q_1$ by reducing the current passed through the coil for the subsequent pulse). Alternatively, both the pulse duration and current can be varied together to control the effective value of q. Methods and apparatus according to this disclosure may also be useful to dynamically change the value of I(t) and/or pulse durations to implement effective adiabatic or composite pulses.

To implement the acquisition sequences described herein, NMR measurement methods and apparatus according to this disclosure, e.g., measurement control 201 may arbitrarily and independently control the current amplitude I(t) of the transmitted pulses. A number of embodiments may be effective to control the current that is passed through the surface coil for each pulse independently; such embodiments may also allow the amplitude of a single pulse to be dynamically varied. In some embodiments, the pulse current may be supplied by switching voltage from one or more DC power supplies with a fixed bus voltage. In such embodiments, two or more separate supplies with different and independent bus voltages can used to supply driving voltage for the two different pulses, thus producing pulses with different amounts of current. Alternatively if there is a single DC power supply, the duty cycle of the AC (Larmor frequency) switched current from the DC supply can be varied between pulses or dynamically during a single pulse to decrease or increase the total rms current for the pulses.

In some embodiments, measurement control 201 may control or change the current between pulses or dynamically during a single pulse, by adjusting the impedance of the transmitting device and/or the transmitting coil or coils. In such embodiments the impedance of the transmitter and/or the coil may be adjusted by adding or subtracting resistive or reactive electronics in the transmitter-coil circuit, e.g., switching a resistive element to selectively couple the resistive element within a transmitting circuit in a surface NMR acquisition apparatus.

In some embodiments, measurement control 201 may control or change the current between pulses or dynamically during a single pulse, by adjusting the difference between the resonant frequency of the coil and the frequency of the driving voltage. As the difference between the driving voltage frequency and the coil resonant frequency increase, the current on the coil will decrease. This approach may be particularly useful for controlling the functions I(t) and f(t) for an adiabatic pulse, where it is often required that the amplitude of I(t) be small when the offset between f(t) and the Larmor frequency $f_0$ is large.

In some embodiments, measurement control 201 may control the effective pulse moment between two pulses by transmitting on two different coils. In this embodiment the large pulse moment of the preparatory pulse is achieved by transmitting on a coil with low impedance and/or a larger number of turns, and the smaller pulse moment of the subsequent pulse is achieved by transmitting on a coil with higher impedance and/or smaller number of turns.

In some embodiments, measurement control 201 may control the effective pulse moment difference between the preparatory and subsequent pulses by using separate transmitters to generate the preparatory and subsequent pulses.

Disclosed methods to dynamically control and vary the amplitude of a signal pulse or to control and vary the relative amplitude of at least two pulses in a multi-pulse sequence may be useful in the field of geophysical surface NMR for measurements different from those described above. For example, some acquisitions may use a single adiabatic pulse where I(t) is dynamically varied. A single adiabatic pulse may be selected to provide excitation of fluids in the subsurface over a wider range of depths than an on-resonance pulse and thus improved signal detection. As another example, a spin-echo pulse sequence may be acquired in which a preparatory excitation pulse has half the amplitude of a subsequent refocusing pulse, so that the subsequent pulse provides twice the effective tip angle as the preparatory pulse. It may be preferable to achieve a double of tip angle by adjusting the relative amplitude of the excitation and refocusing pulses; instead adjusting their relative duration would change the effective bandwidth of the two pulses.

In some embodiments, the phase of the transmitted pulses may be controlled in order to eliminate particular signal artifacts that are undesired. Specifically for embodiments of the CR acquisition scheme, signal artifacts that are not associated with the FID2 signal that are generated by the subsequent depth-profiling pulse may be eliminated. These artifacts can potentially include NMR or non-NMR signals that share phase coherence with the transmitted pulses. Specifically, for the CR sequence, artifacts associated with residual transverse magnetization from the preparatory pulse and non-NMR artifacts associated with the subsequent pulse may be effectively cancelled. A phase cycling strategy can be implemented to mitigate such artifacts.

In some embodiments of phase cycling for the CR sequence, acquisitions in which the phase of the pulses are varied, but all other parameters are kept identical may be repeated and combined to improve signal to noise and to suppress artifacts. To achieve artifact suppression by phase cycling for a single CR acquisition, two identical acquisitions may be acquired, referred to as A and B. The phase of the preparatory pulse in both sequences may be fixed between acquisition A and B; the subsequent pulse may have a value of $\varphi_2$ in acquisition A and a value of $\varphi_2+180°$ in acquisition B. Data for the two acquisitions may then be linearly combined by subtracting the data for acquisition B from the data for acquisition A. The result is that undesired artifacts that have constant phase between both acquisitions are cancelled, including (i) NMR signals representing residual transverse magnetization from the preparatory pulse and (ii) non-NMR signals that are associated with the hardware artifacts after the subsequent pulse. NMR signals that have a 180° phase shift between the acquisitions are preserved, specifically the component of the FID2 signal associated with recovered longitudinal magnetization.

Some embodiments may use more than two pulses to allow detection of NMR spin echo signals used to further estimate the $T_2$ relaxation time, and its covariance with $T_1$ and $T_2^*$, as a function of subsurface position. In one such embodiment, that may be termed "crush-recovery spin-echo" (CRSE), a set of multi-pulse acquisition sequences may comprise a collection of multi-pulse acquisition sequences, wherein at least three pulses are used in each multi-pulse acquisition sequence. The preparatory crushing pulse may be on-resonance, adiabatic, or composite and at least two on-resonance subsequent pulses may have values of $q_2$, $q_3$, where the value of $q_3$ is 0.75 to 2.5 times the value of $q_2$. A second pulse may be referred to as the "depth sensitive pulse" and a third pulse may be referred to as the "refocusing pulse". The delay time between the preparatory and second pulse may be called $\tau_{d1}$, and the delay time between the second and third pulse may be called $\tau_{d2}$. In at least one of the multi-pulse acquisition sequences in the set, the properties of the crushing pulse are constant, the value of $\tau_{d1}$ is constant, and maximum excitation depth of the second pulse is substantively less than that of the preparatory pulse. In such an embodiment, the preparatory pulse may act to crush the magnetization within a range of subsurface depths where later pulses provide sensitivity to NMR FID and spin echo signals. Spin echo signals may be observed following the third (refocusing) pulse.

Figure 6:
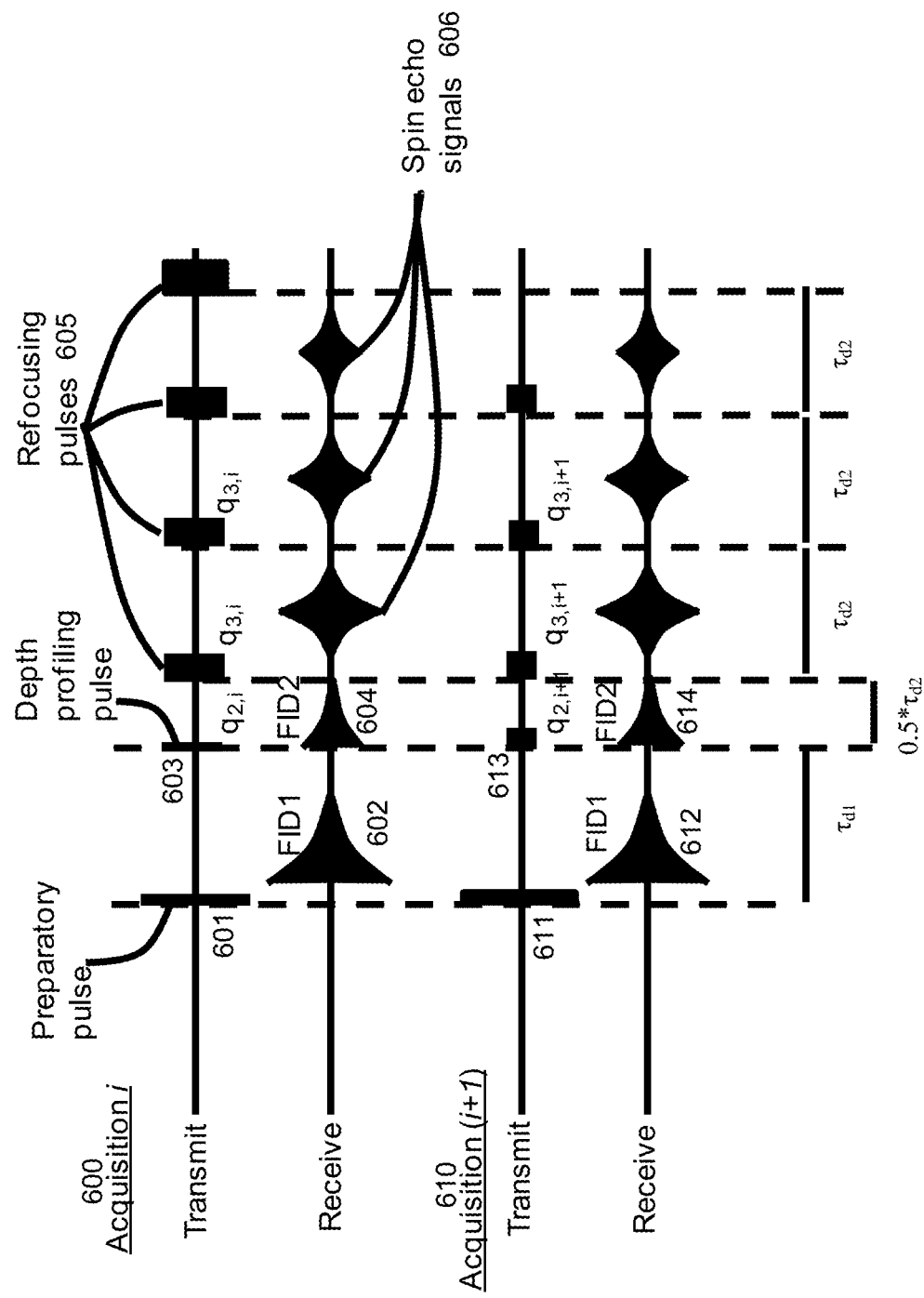
FIG. 6 illustrates an example crush recovery CPMG sequence.

FIG. 6 illustrates a NMR acquisition in which additional refocusing pulses may be transmitted in an acquisition sequence and a train of spin echo signals may be recorded between the refocusing pulses. Such an embodiment may be referred to as a Crush-Recovery Carr-Purcell-Meiboom-Gill (CRCPMG) sequence. FIG. 6 may generally be understood with reference to FIG. 5A, above. FIG. comprises an acquisition i 600 and an acquisition i+1 610, wherein acquisition i 600 comprises transmit operations 601 and 603, as well as refocusing pulses 605, and receive operations 602 and 604, as well as receive operations for spin echo signals 606. Acquisition i+1 610 comprises transmit operations 611 and 613, as well as refocusing pulses analogous to refocusing pulses 605 in acquisition i, and receive operations 612 and 614, as well as receive operations for spin echo signals as illustrated. In FIG. 6, the preparatory pulses 601 and 611 and depth profiling pulses 603 and 613 may be according to any of FIG. 5A, 5B, or 5C.

In embodiments according to FIG. 6, the refocusing pulses 605 in a single acquisition such as acquisition i 600 may have similar pulse moments $q_3$. The time delays between each refocusing pulse $\tau_{d2}$ may be similar for the single acquisition and between acquisitions, with varied values of $q_2$ and $q_3$ between acquisitions, that is, varied pulse moments for depth profiling pulses 603 and 613, and varied pulse moments for refocusing pulses 605 and the refocusing pulses of acquisition i+1 610. In some embodiments, the time delay between a depth profiling pulse 603 and a first refocusing pulse 605 may be approximately $0.5 * \tau_{d2}$. A complete CRCPMG dataset may comprise multiple acquisitions between which the value of q2, q3, $\tau_{d1}$, and $\tau_{d2}$ are varied.

Processing of Surface NMR Signals

Various processing approaches can be used to process data acquired following the above embodiments to estimate the spatial variation in fluid content and relaxation times in the subsurface. The below outlined approaches to estimate fluid content, $T_2^*$, and $T_1$ in the subsurface are made possible because of two unique characteristics of the aforementioned CR acquisition scheme: (i) the initial longitudinal magnetization is effectively crushed prior to application of the subsequent pulse, and (ii) the initial conditions prior to application of the depth-sampling pulse are consistent across any set of single acquisitions for which the properties of the preparatory pulse and $\tau_d$ are fixed. As a result, it is possible to use a standard NMR mathematical inversion kernel described in prior art to isolate the signal associated with the recovered longitudinal magnetization as a function of depth.

Figure 7:
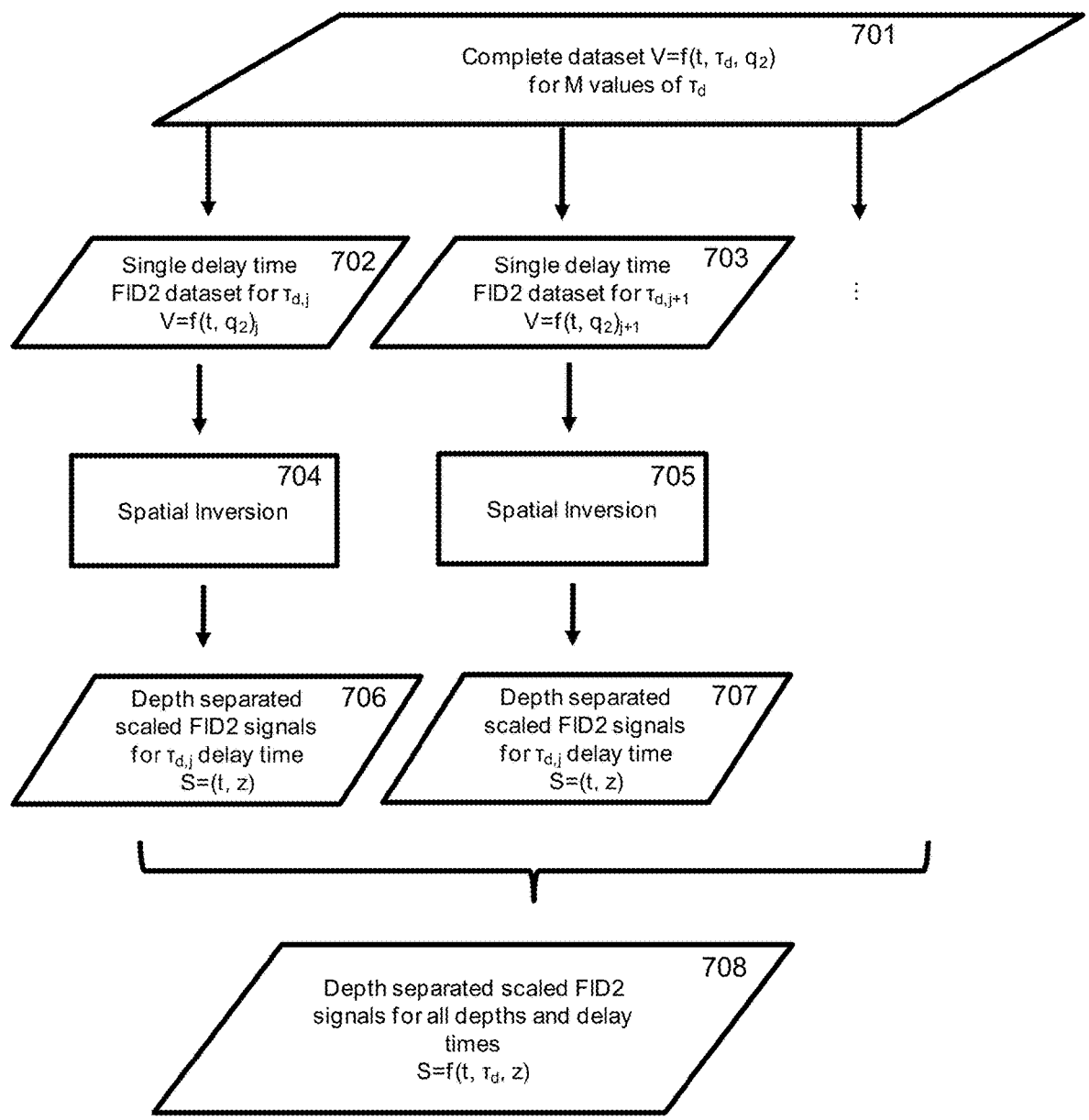
FIG. 7 is a flowchart illustration of example pre-processing and spatial inversion methods for data acquired using a crush recovery sequence.
Figure 8:
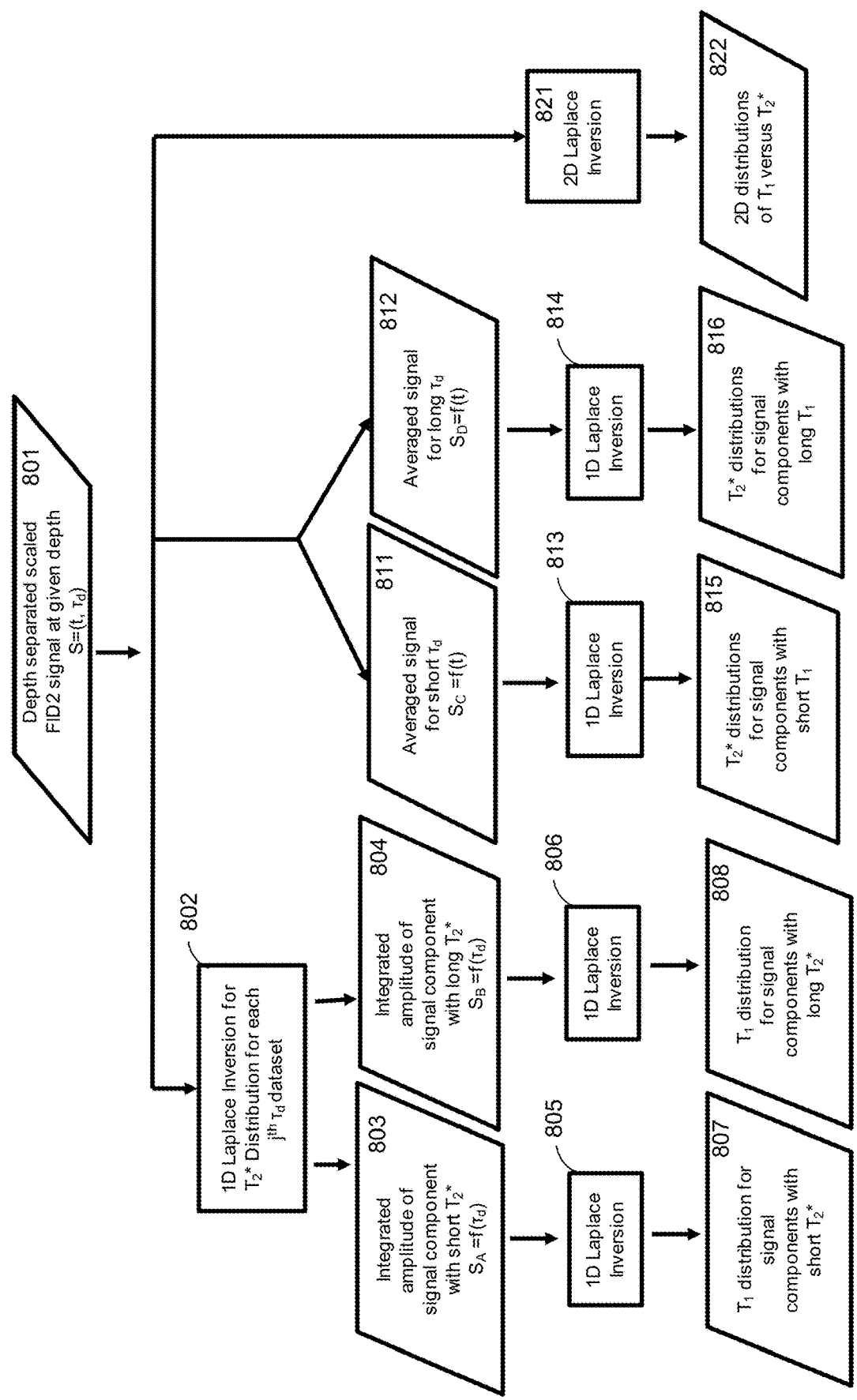
FIG. 8 is a flowchart illustration of example processing methods for estimating $T_1$ and $T_2^*$ parameters following pre-processing and spatial inversion of crush recovery data.

In some embodiments, a complete CR dataset can be processed in several stages, as shown in FIG. 7 and FIG. 8. FIG. 7 and FIG. 8 represent operations which may be performed in accordance with example methods, processing operations and/or functional modules which may be implemented in a computing device, and instructions which may be recorded on a computer readable medium.

Referring to FIG. 7, the complete CR dataset 701 may comprise a collection of voltage signals $V(t, \tau_d, q_2)$, such as 702, 703, and any other voltage signals, with M values of rd. The CR dataset 701 may be separated into M single delay-time datasets $V(t, \tau_d=\tau_{d,j}, q_2)$ 702, 703, etc. A mathematical spatial inversion may be performed for each jth dataset at blocks 704, 705, etc., to derive scaled position or depth-separated signal $S(t, \tau_d=\tau_{d,j}, z=z_k)$ represented by data items 706, 707, etc., for each depth layer a in the subsurface. Here the $S(t, \tau_d=\tau\tau_{d,j}, z=z_k)$ signals 708 represents the FID2 response associated with the component of the longitudinal magnetization that has recovered by $T_1$ over a delay time of $\tau_{d,j}$ at a depth interval $z_k$. The $S(t, \tau_{d,j}, z)$ signals 708 may also be scaled during the inversion so that they reflect the volumetric water content at each depth. The mathematical inversion may alternatively operate in two or three spatial dimensions to estimate the scaled signals as a function of the location of finite volume elements.

In some embodiments, the aforementioned mathematical spatial inversion may follow a linear inversion using a standard forward modeling kernel K(r,q) where r is a subsurface position (or K(z, q) in 1D) which is used for standard NMR single-pulse FID measurements. It should be noted that the use of the standard kernel is possible at least in part because the initial conditions prior to the application of the subsequent pulse are identical for all acquisition sequences where $q_1$ and $\tau_d$ are fixed. Attempting to use the same approach to invert data acquired using a PSR sequence may produce erroneous results because the initial conditions prior to the application of the subsequent pulse may vary as the q-value of the subsequent pulse varies (because the q-value of the preparatory pulse also changes). Other signal conditioning processes including the application of noise cancellation or phase compensation may be applied at any stage before or during the spatial inversion step.

In some embodiments, a spatial inversion of a CRSE or CRCPMG dataset may follow a similar procedure as was outlined above for the CR dataset, wherein the forward model kernel for the FID signal is replaced by a forward model kernel for a spin-echo signal. The output of such a mathematical inversion may be spin echo signals $S(z, t, \tau_{d1}, \tau_{d2})$ estimated as a function of depth.

Returning to the CR dataset, given the spatially inverted FID2 signals for a given depth $S(t, \tau_d)$ there are various approaches that can be used to estimate the relaxation times, multi-exponential distributions of relaxation times, and the covariance of the relaxation times. Various embodiments for estimating $T_2^*$ and $T_1$ from a crush recovery dataset are illustrated in a schematic flow chart in FIG. 8.

In some embodiments, the $S(t, \tau_d=\tau_{d,j})$ signal 801 for each jth delay time at each depth may be processed using a 1-dimensional Laplace inversion 802 to determine a $T_2^*$ distribution. Each $T_2^*$ distribution is then subdivided into bins such as 803 and 804, classifying short $T_2^*$ 803 or long $T_2^*$ 804 signals according to a specified cut-off value of $T_2^*$. For each delay time, the integrated amplitude of the signal is calculated for the short $T_2^*$ bin $S_A(\tau_d)$ and the long $T_2^*$ bin $S_B(\tau_d)$. The resulting $S_A(\tau_d)$ and $S_B(\tau_d)$ curves may be processed separately using a single-exponential fit or Laplace inversion in blocks 805 and 806 to determine the fluid volume and $T_1$ characteristics of NMR signals having short $T_2^*$ values 807 separately from the fluid volume and $T_1$ characteristics of NMR signals having long $T_2^*$ values 808. Alternatively, the $T_2^*$ distributions can be separated into more than two bins (e.g. three bins to independently classify signals with short, intermediate, and long $T_2^*$ decay times, or any arbitrary number of subdivided bins).

In some embodiments, a finite number of decay time bins equal to or smaller than the total number of delay time datasets may be specified, and the $S(t, \tau_d)$ signals for which $\tau_d$ is within each specified bin range may be combined by linear averaging. For example a signal $S_C(t)$ may be computed by averaging signals with a given range of short $\tau_d$ at block 811 and a subsequent signal $S_D(t)$ may be computed by averaging the signals with a given range of long delay times at block 812. The resulting $S_C(\tau_d)$ and $S_D(\tau_d)$ curves may then be processed separately using a single-exponential fit or Laplace inversion at blocks 813, 814 to determine the fluid volume and $T_2^*$ characteristics of NMR signals having short $T_1$ values 815 separately from the fluid volume and $T_2^*$ characteristics of NMR signals having long $T_1$ 816. Alternatively, the $S(t, \tau_d)$ signals may be divided into any number of bins less than the total number of delay times acquired in the complete dataset.

In some embodiments, the $S(t, \tau_d)$ signals can be processed to simultaneously estimate the a two-dimensional distribution of $T_2^*$ versus $T_1$. Generally, the $S(t, \tau_d)$ can be represented by the following function assuming a multi-exponential relaxation behavior:

$$S(t, \tau_d) \int \int w(T_2^*, T_1) e^{-\frac{t}{T_2^*}} \left(1 - e^{-\frac{\tau_d}{T_1}}\right) dT_2 dT_1$$

In some embodiments, a two-dimensional Laplace inversion of the $S(t, \tau_d)$ can be used at block 821 to estimate the two-dimensional distribution and covariance of $T_2^*$ and $T_1$ at a given depth, shown at block 822. An advantage of such embodiments is that it is possible to impose constraints on the covariance of $T_2^*$ and $T_1$. For example a constraint can be exercised that the value of $T_1$ must be greater than the value of $T_2^*$, as is known to be required by NMR physics. Further, it is possible to specify a bound on the value of $T_1$, the value of $T_2^*$, or on the ratio of $T_1$ to $T_2^*$, which can improve the stability of the inversion. Specifying bounds in the manner also enables dense sampling and precision of the $T_2^*$ decay process (set by the dense data sampling rate of the NMR voltage recording) to improve that the temporal resolution of the $T_1$ decay process, which is sparsely sampled in time (given a finite number of $\tau_d$ values).

In some embodiments, data may be acquired using a CRCPMG sequence and used to estimate the two-dimensional covariance distribution of $T_1$ and $T_2$. In such an embodiment the spatially inverted data $S(t, \tau_{d1})$ for a fixed value of $\tau_{d2}$ may first be analyzed to determine the amplitude of each spin echo signal $S_{echo}$ recorded at the center time t between refocusing pulses and for each value of $\tau_{d1}$ in the full set of acquisitions. A two-dimensional Laplace inversion of the resulting dataset $S_{echo}(t, \tau_{d1})$ may then be used to estimate the two-dimensional distribution and covariance of $T_2$ and $T_1$ at a given depth. The decay time $T_D$ associated with diffusion of the fluid is a function of the delay time between refocusing pulses ($\tau_{d2}$). Thus if acquisitions with varied values of $\tau_{d2}$ are included in the set, the resulting dataset $S_{echo}(t, \tau_{d1}, \tau_{d2})$ may be used with a three-dimensional Laplace inversion to determine a three-dimensional covariance distribution of $T_1$ $T_2$ and $T_D$. $T_1$, $T_2^*$, $T_2$, $T_D$, and their spatial distribution in the subsurface derived by the above methods may be used to estimate other properties, including fluid, geologic, hydrogeologic, mineralogic, or biogeologic properties. For example $T_1$ and $T_2$ can be highly sensitive to fluid viscosity, pore size, permeability, and surface mineralogy and so can be used to estimate these properties. Also $T_D$, $T_2^*$, and the ratio of $T_2^*:T_1$ or $T_2:T_1$ may be sensitive to the magnetic properties of the formation and diffusion coefficient of the fluid.

In some embodiments, surface NMR apparatus and subsurface characterization techniques provided herein may be applied to image NMR properties at positions in the subsurface. In some embodiments, NMR apparatus and subsurface characterization techniques provided herein may be applied to image and estimate NMR relaxation times at positions in the subsurface, which can be related to subsurface properties of interest, including pore size and permeability. In some embodiments, NMR apparatus and subsurface characterization techniques provided herein may be applied to estimate relaxation times and to provide improved estimation and imaging of the $T_1$ relaxation at positions in the subsurface. In some embodiments, NMR apparatus and subsurface characterization techniques provided herein may be applied to provide improved estimation and imaging of the covariance of more than one relaxation time at positions in the subsurface. In some embodiments, NMR apparatus and subsurface characterization techniques provided herein may be applied to provide estimation of more than one relaxation time and their covariance as a function of depth from surface NMR measurements.

In the foregoing description, adiabatic pulse and composite pulses are described, wherein, the pulse phase $\varphi(t)$, pulse frequency $f(t)$ and/or pulse current $I(t)$ are changed during the pulse. Pulses in which the pulse phase $\varphi(t)$, pulse frequency $f(t)$ and/or pulse current $I(t)$ are changed during the pulse may be referred to herein as modulated pulses. In contrast, a standard on-resonance pulse is not a modulated pulse, because the phase, frequency, and current are nominally fixed throughout the pulse duration. A useful feature of modulated pulses, in comparison to non-modulated, on-resonance pulses, is that modulated pulses can provide excitation of fluids in the subsurface over a wider range of depths than non-modulated pulses, leading to improved signal detection, as noted herein. This is because modulated pulses, and adiabatic and composite pulses in particular, may be designed to excite coherent transverse magnetization over a wider range of $B_1$ values than can be achieved with non-modulated pulses. For a surface-NMR measurement in which $B_1$ fields are generated by a coil at the surface, this feature of adiabatic and composite pulses allows coherent transverse magnetization of fluids to be excited over a larger subsurface volume where the $B_1$ fields are highly heterogeneous. For example, for a typical surface coil (e.g., a coil with a 50 meter diameter) which may be used to measure a subsurface volume having a depth which is generally equivalent to the diameter of the surface coil (e.g. a depth of 50 meters), modulated pulses may be used to excite transverse magnetization in up to 80% or more than the depth of the subsurface volume, with corresponding improvements in measurement quality.

In some previously described embodiments, the ability of an adiabatic or composite pulse to coherently excite transverse magnetization over a large volume is utilized in a two pulse sequence: the adiabatic or composite pulse is transmitted as an initial, preparatory pulse, which nulls longitudinal magnetization, and is followed by a second pulse that is transmitted after a brief delay. In such embodiments the transverse magnetization resulting from the second pulse is measured and is related to the magnetization that recovers by $T_1$ processes during the delay between the pulses.

In other previously described embodiments, single-pulse measurement schemes may be used in which an acquisition sequence may comprise transmitting one single pulse, and then recording the subsequent NMR FID signal as one or more voltage measurements. As also noted herein, the single pulse may comprise an adiabatic pulse (which is an example of a modulated pulse), selected to provide excitation of fluids in the subsurface over a wider range of depths than an on-resonance pulse and thus improved signal detection. In such single-pulse measurement schemes involving modulated pulses, the transverse magnetization excited directly by the adiabatic or composite pulse itself may be measured. Detecting the transverse magnetization excited by the adiabatic or composite pulse may be desirable because a larger volume is excited, resulting in a larger signal amplitude and an ability to simultaneously detect fluids over a wider range of depths and positions.

Figures 9A, 9B, 9C:
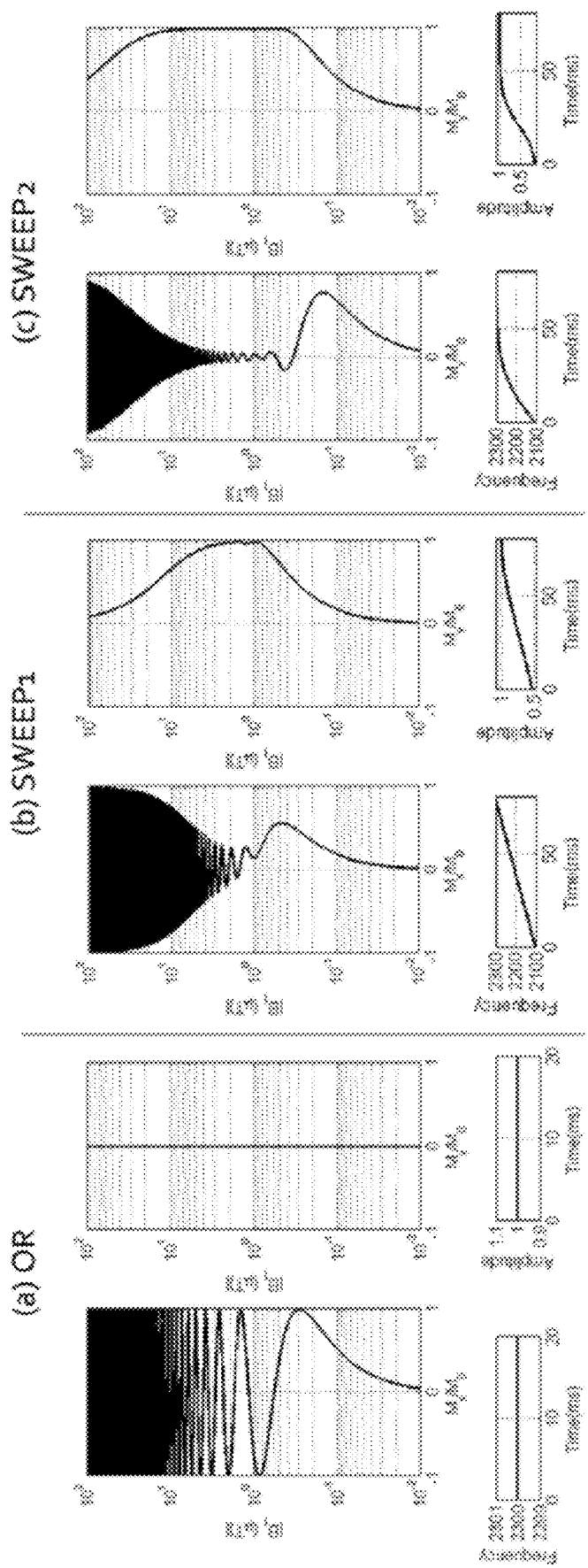
FIG. 9A, FIG. 9B, and FIG. 9C are graphs illustrating example excitation of transverse magnetization as a function of $B_1$ field strength for an on-resonance pulse and two adiabatic pulses.

FIGS. 9A, 9B, and 9C are graphs illustrating example excitation of transverse magnetization as a function of $B_1$ field strength for three different types of pulses with different amplitude and frequency modulation: an on-resonance pulse and two adiabatic pulses. FIG. 9A illustrates an on-resonance pulse with no amplitude or frequency modulation, FIG. 9B illustrates an adiabatic pulse SWEEP1 with substantial amplitude and frequency modulation, and FIG. 9C illustrates an adiabatic pulse SWEEP2 with a different substantial amplitude and frequency modulation. In all cases, the Larmor frequency is 2300 Hz and all the pulses have a frequency substantially equal to this value at the end of the pulse. In each of FIGS. 9A, 9B, and 9C, the bottom two graphs show the frequency and amplitude of the applied pulse. The upper two graphs show the resulting excited transverse magnetization as a function of the $B_1$ field amplitude. The upper left graph shows the component of the magnetization excited into the x-direction (parallel to the phase of the pulse), and the upper right graph shows the component of the magnetization excited into the y-direction (perpendicular to the phase of the pulse).

For the on-resonance pulse in FIG. 9A, the magnetization is entirely in the positive and negative x directions; no magnetization is excited in the y-direction. The excitation profile shows rapidly varying oscillations at high $B_1$ values, producing incoherent excitation. Significant coherent excitation is only produced at intermediate $B_1$ values where there is a main lobe of transverse magnetization is excited in the positive x-direction. Regarding the width of this main lobe, the value of $M_x/M_0$ is greater than 0.5 only for $B_1$ values between ~0.1 µT and 0.5 µT. For the SWEEP1 adiabatic pulse in FIG. 9B, coherent excitation is primarily in the y-direction. There is coherent excitation of magnetization in the positive y-direction for a much wider range of $B_1$ values than in FIG. 9A; and $M_y/M_0$ is greater than 0.5 between ~0.3 µT and 15 µT. In the x-direction there is a narrow zone of coherent excitation from ~0.3 µT and 0.7 µT. For the SWEEP2 adiabatic pulse in FIG. 9C, the range of coherent excitation in the y-direction is even wider than in FIG. 9B; and $M_y/M_0$ is greater than 0.5 between ~0.1 µT and 60 µT.

The difference in the excitation pattern between the SWEEP1 and SWEEP2 pulse is due to the fact that the frequency and amplitude modulation functions differ between the two pulses. In the SWEEP1 pulse, the frequency is changed in a linear sweep from 200 Hz below resonance to on resonance during the 80 ms pulse. In the SWEEP2 pulse, the frequency is also swept over 200 Hz in 80 ms but changes more rapidly at the start of the pulse and more slowly at the end of the pulse. Also, the amplitude modulation function for SWEEP2 begins at a lower value than SWEEP1 and rises more abruptly than SWEEP1.

FIGS. 10A, 10B, and 10C are graphs illustrating example excitation as a function of position beneath a surface NMR coil for one on-resonance pulse and two adiabatic pulses. FIGS. 10A, 10B, and 10C illustrate the effect of these pulses in exciting transverse magnetization in a surface-NMR measurement. FIGS. 10A, 10B, and 10C illustrate spatial excitation patterns in the subsurface resulting from each of the previous three pulses, shown again with $M_x$ and $M_y$ components. In FIGS. 10A, 10B, and 10C, the surface coil is a 40 m two-turn circular loop, but other loop dimensions may be used (e.g. larger loops for deeper investigation depth, or smaller for shallower investigation depth). In FIG. 10A, the excitation pattern for the on-resonance pulse illustrates that the subsurface is excited in a very non-uniform manner with rapid oscillations between positive $M_x$ and negative $M_x$ values. These oscillations result in a transverse magnetization that has low coherence and produces a relatively low detectable NMR voltage signal on the surface coil.

In FIG. 10B, the excitation pattern produced by the adiabatic SWEEP1 pulse produces a large volume of coherent excitation in the $M_y$ component. For the SWEEP2 pulse in FIG. 10C, the excitation pattern in the $M_y$ component is even more uniform. The SWEEP2 pulse also produces a deep component of coherent magnetization with an $M_x$ component (i.e. between 40 m and 60 m).

Figure 11B:
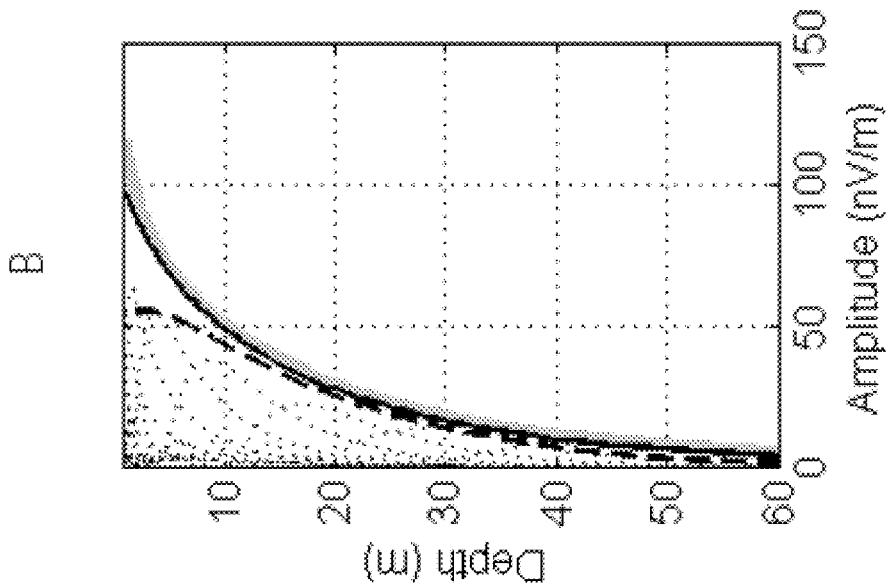
FIG. 11A and FIG. 11B are graphs illustrating example surface NMR signal amplitudes as a function of pulse current for different pulse types.
Figure 11A:
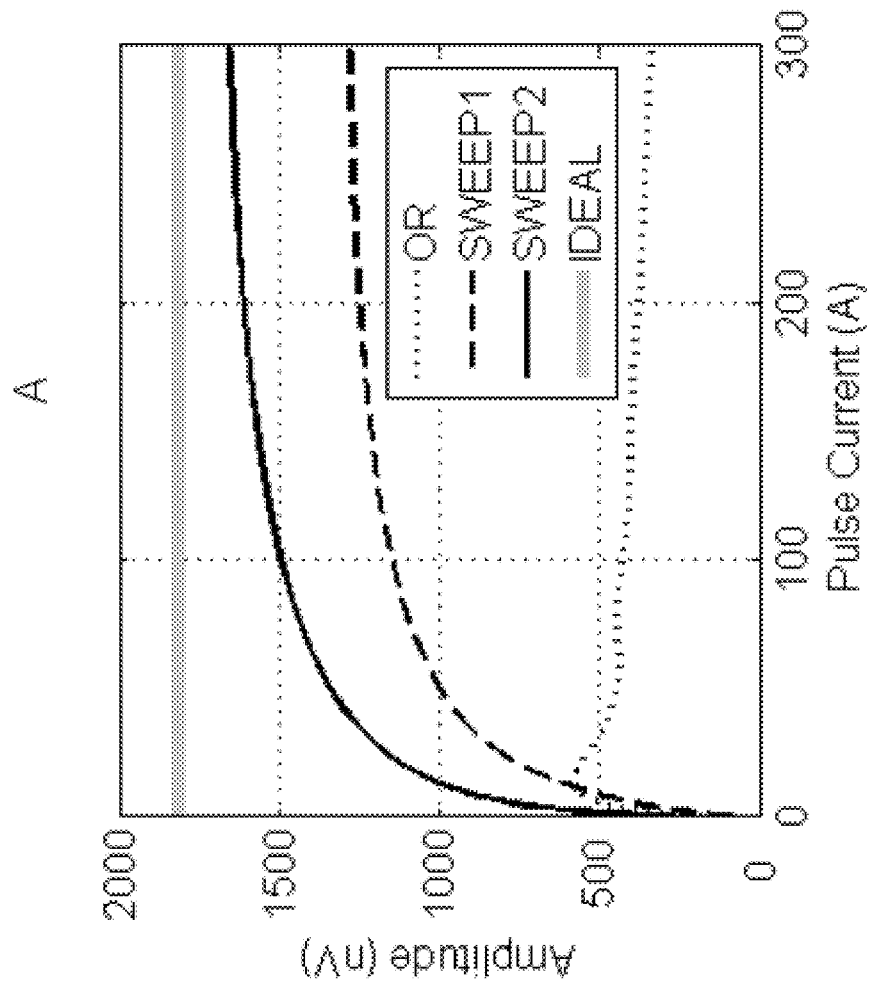

FIGS. 11A and 11B are graphs illustrating example surface NMR signal amplitudes as a function of pulse current for different pulse types. One advantage of larger excited volumes is that larger NMR signals will be generated and detected on the surface coil. FIGS. 11A and 11B show the NMR signal amplitude that would result from measuring (using the surface coil) the transverse magnetization excited by each of the pulses discussed above. For comparison, FIGS. 11A and 11B also show the amplitude of the signal that would be detected for an "ideal" pulse that provided excitation across the entire subsurface volume. FIG. 11A shows the detected signal amplitude in nV (y-axis) as a function of the peak transmit amplitude (i.e. the value of I(t) at the end of the pulse); the values are scaled to represent a subsurface with 25% water content from the surface to an depth of 80 m. The adiabatic pulses produce a peak signal amplitude that is 2-3 times larger than peak signal amplitude for the on-resonance pulse. For the adiabatic pulses, the maximum voltage occurs at the highest pulse currents when the excited volume extends from the surface to a maximum depth. For the on-resonance pulse, the maximum current peaks at a specific current value ~15 A, and is significantly lower as the pulse amplitude is increased or decreased. This characteristic reflects the fact that the on-resonance pulse coherently excites a smaller volume of the subsurface; a maximum amplitude is detected only when the pulse current is matched to produce excitation over a volume where the coil is most sensitive. In contrast, the adiabatic pulses excite a large volume of the subsurface, and at a high pulse current value, maximum coherent transverse magnetization is excited over almost the entire volume of the subsurface to which the coil is sensitive.

FIG. 11B shows the depth sensitivity for each of the pulses; plotted is the NMR signal amplitude (x-axis) that would be detected on the coil for a 1 m thick layer with 25% water content at a given depth level (y-axis). The multiple dotted lines show depth sensitivity for the on-resonance pulse for five different cases where the pulse current is 1 A (shallowest sensitivity), 5 A, 25 A, 125 A, and 600 A (deepest sensitivity). This result illustrates that for on-resonance pulses, multiple measurements must be performed with different pulse current amplitudes to obtain sensitivity to water at different depth levels. In contrast, the dashed and solid black lines show the depth sensitivity for the SWEEP1 pulse and SWEEP2 pulse, respectively, when a high peak current amplitude of 300 A is used. Here a measurement using a single adiabatic pulse transmitted with a high amplitude provides sensitivity to water over the full range of depths. In contrast to the on-resonance measurement, only one adiabatic pulse need be conducted to achieve equivalent sensitivity to water over a wide range of depths.

Figure 12:
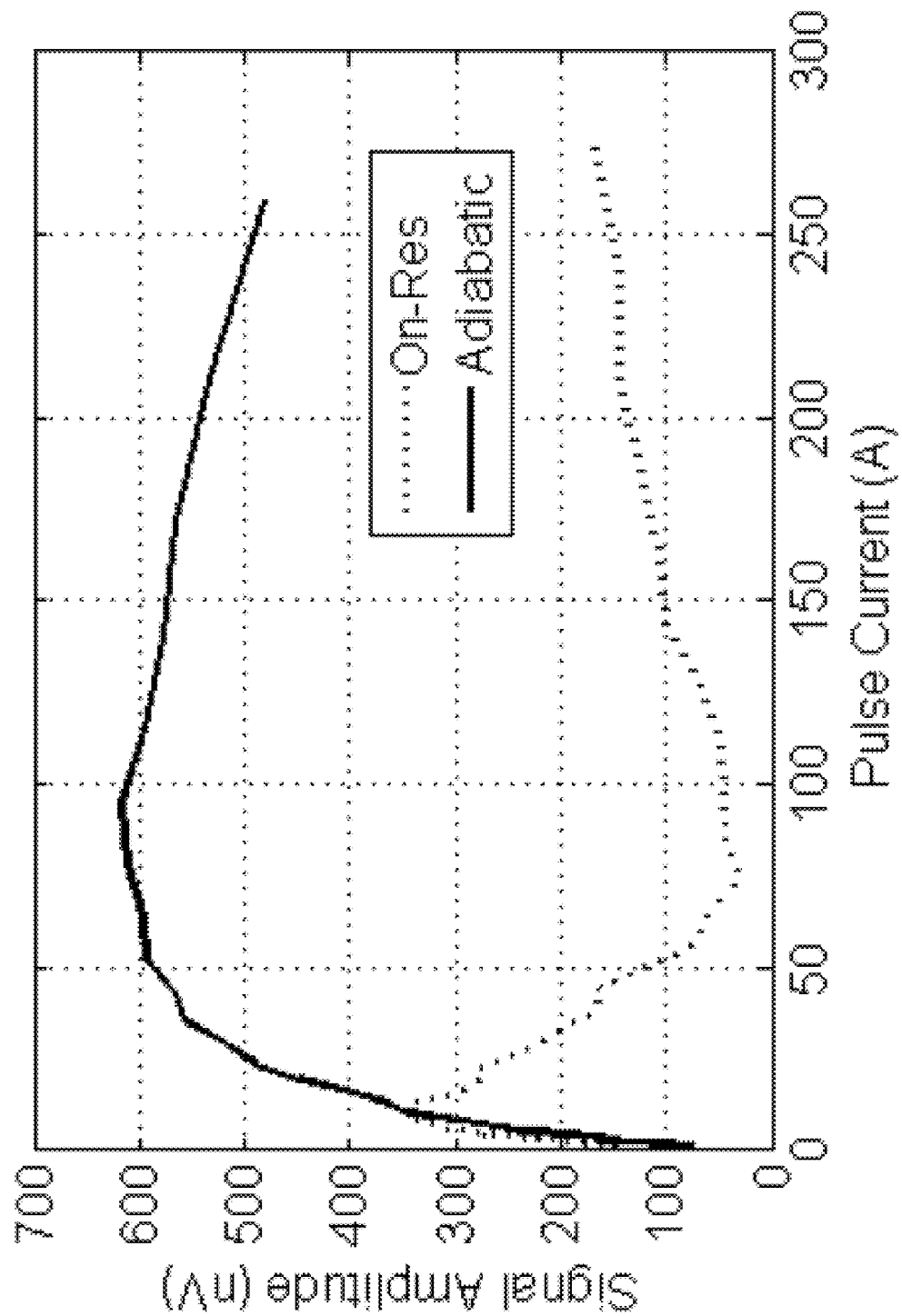
FIG. 12 is a graph illustrating example surface NMR signal amplitudes as a function of pulse current using different pulse types for actual field data.

FIG. 12 is a graph illustrating example surface NMR signal amplitudes as a function of pulse current using different pulse types for actual field data. FIG. 12 shows data from real field measurements comparing a 20 ms on resonance pulse to a 80 ms adiabatic pulse with parameters similar to SWEEP1. Pulses were transmitted with a range of peak pulse currents. Data were acquired using the hardware and methodologies described herein. Graphed is the NMR signal amplitude as a function of the peak pulse current for the on-resonance pulse (dotted) and the adiabatic pulse (solid). These data show that indeed the adiabatic pulse produces significantly larger transverse magnetization signal voltage than the on-resonance pulse. The adiabatic pulse transmitted with high peak current has a significantly higher amplitude because it simultaneously excites the subsurface over a wide range of depths.

Given advantages of an adiabatic pulse and corresponding advantages of modulated pulses in general, in some embodiments of the invention, an adiabatic or other modulated pulse with a relatively high pulse current might be used to substantially uniformly excite a relatively large volume of the subsurface. The substantially uniform transverse magnetization resulting from the adiabatic or other modulated pulse may be measured to simultaneously detect fluids that may occur over a relatively wide range of depths. This approach is advantageous in that it produces NMR signal amplitudes that may be significantly larger than (e.g., more than twice as large as) the signal amplitudes that would be generated using an on-resonance pulse, and this approach allows investigation over a wide range of depths.

For example, for a 50 m diameter surface coil, an adiabatic or other modulated pulse with a pulse current of 100 A or greater, or in some embodiments 200 A or greater, may be used to substantially uniformly excite the volume beneath the 50 m surface coil at depths from 0 m (directly underneath the coil) to 80% or otherwise substantially the entire 50 m depth under the surface coil. Proportional pulse currents and excitation volumes may be produced in other size surface coils.

Figure 13:
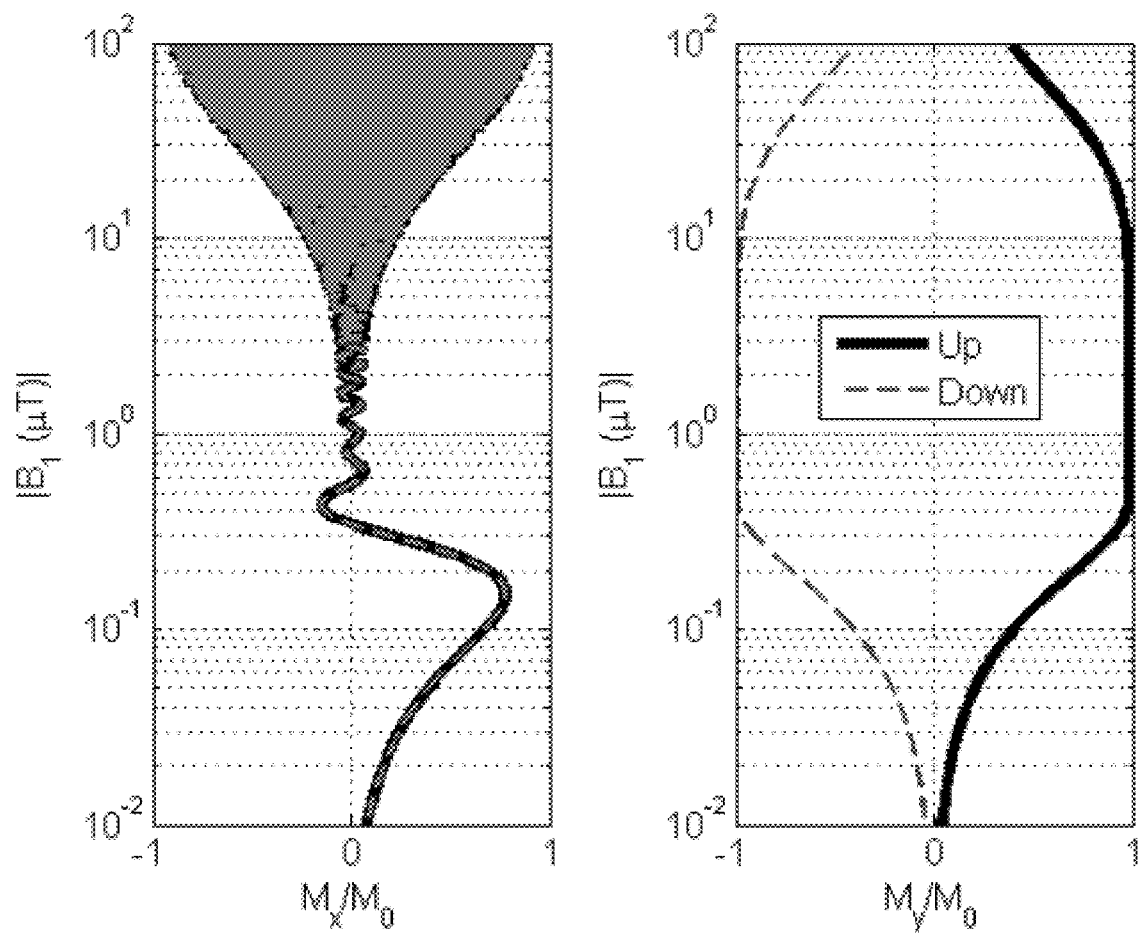
FIG. 13 is a graph illustrating example separation of x- and y-components of excited magnetization for an adiabatic pulse produced by changing the sweep direction.

FIG. 13 is a graph illustrating example separation of x- and y-components of excited magnetization for an adiabatic pulse produced by changing the sweep direction. As noted in the discussion of FIGS. 9 and 10, an adiabatic pulse excites some magnetization with an $M_y$ component and some magnetization with an $M_x$ component. As shown FIG. 10, the x- and y-components excite water at different depths. In some embodiments it may be useful to separate these x- and y-components, for example to localize the sensitivity of the measurement to a particular depth. FIG. 13 illustrates a method to separate these components using two acquisitions. In the first acquisition, an adiabatic pulse is transmitted where the frequency is swept from below resonance in an 'up' direction to the Larmor frequency and produces the excitation patterns shown as solid lines. In the second acquisition, an adiabatic pulse is transmitted where the frequency is swept from above resonance in a 'down' direction to the Larmor frequency and produces the excitation patterns shown as dashed lines. Comparing the excitation patterns of these two pulses, it is observed that the $M_x$ components are the same between the pulses and the $M_y$ components have opposite sign between the pulses. Therefore, the measurements will produce signals with identical x-components and with y-components of opposite signs. By subtracting the signals, the x-component is cancelled and only the y-component is retained. By adding the signals, the y-component is cancelled and the x-component is retained. In some embodiments, the separated $M_x$ and $M_y$ components may be used to determine the distribution of fluids and their NMR relaxation times as a function of depth and position.

Composite pulses have similar characteristics as adiabatic pulses, in that they produce excitation over a wider range of $B_1$ values and depth than an on-resonance pulse. Thus, in some embodiments, the transverse magnetization resulting from composite pulses may be measured to detect fluids that may occur over a wide range of depths. In other words, in some embodiments, the techniques described herein which use adiabatic pulses may instead use composite pulses or other modulated pulses.

Detection of the transverse magnetization resulting from an adiabatic or composite pulse may further be used to localize the position of signals from subsurface fluids and to determine their relaxation times. In some embodiments, a series of measurements may be conducted using adiabatic and/or composite pulses with different peak current amplitudes, phase modulation, frequency modulation, and or amplitude modulation to produce excitation patterns with varied depth and spatial geometries. A mathematical inversion of these measurements may then be used to determine the location of subsurface fluids as a function of depth, and to determine their abundance, and relaxation time parameters.

In some embodiments an adiabatic or composite pulse may be transmitted on a main transmission coil and the resulting transverse magnetization signal may be measured on multiple receive coils located within the main loop or nearby the main loop such. The one or more receive coils may be positioned and sized such that they are sensitive to different volumes of the subsurface. As such, the signals measured on the multiple receive coils may be combined in a mathematical inversion to isolate signals as a function of depth and position in order to generate a 2D or 3D image of subsurface fluids, their abundance, and their NMR relaxation times.

In some other embodiments, a single coil or an array consisting of multiple coils as described above may be moved across the ground surface. Measurements may be repeated in which an adiabatic or composite pulse is used to excite transverse magnetization and one or more coils are used to detect the transverse magnetization resulting from the pulse. By repeating the measurement at many positions over an area, a 2D or 3D map may be generated of subsurface fluids, their abundance and their NMR relaxation times. Because the adiabatic and composite pulses can produce NMR signals that are significantly larger in amplitude than on-resonance pulses, it is possible to implement this mapping more quickly than would be possible with an on-resonance pulse.

In some other embodiments an adiabatic pulse or composite pulse may be used as an initial excitation pulse and followed by refocusing pulses to measure a spin echo or CPMG signal consisting of multiple echoes. In this case, the measured echoes reflect energy excited by the initial adiabatic or composite excitation pulse, which is refocused by the secondary pulses. The refocusing pulses may be on-resonance pulses or may be adiabatic refocusing pulses or composite refocusing pulses. Measuring the refocused echo signals may allow determination of the $T_2$ relaxation time parameter.

There is little distinction left between hardware and software implementations of aspects of systems; the use of hardware or software is generally (but not always) a design choice representing cost vs. efficiency tradeoffs. There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be within the skill of one skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically couplable, physically interacting, wirelessly interacting, and/or logically interacting components.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various embodiments have been disclosed herein, other aspects and embodiments will be apparent to those skilled in art.

The invention claimed is:

1. A surface Nuclear Magnetic Resonance (NMR) measurement method comprising:
performing at least one acquisition sequence with a surface coil using Earth's magnetic field as a static background field, the acquisition sequence comprising:
transmitting at least one initial modulated pulse with the surface coil, wherein at least an amplitude of the initial modulated pulse is varied during the initial modulated pulse, and wherein the initial modulated pulse excites a transverse magnetization component within a subsurface fluid;
wherein the amplitude of the initial modulated pulse is varied during the initial modulated pulse by controlling a current amplitude I(t) of the initial modulated pulse in the surface coil; and
recording an NMR signal associated with the transverse magnetization component excited by the initial modulated pulse on at least one receiving device.

2. The method of claim 1, wherein the at least one initial modulated pulse produces coherent transverse magnetization over a larger subsurface volume than would be generated by a pulse with fixed frequency, amplitude, and phase.

3. The method of claim 1, wherein the initial modulated pulse is an adiabatic pulse.

4. The method of claim 1, wherein a phase or frequency of the initial modulated pulse is varied during the initial modulated pulse.

5. The method of claim 1, wherein the initial modulated pulse is a composite pulse in which a phase of the initial modulated pulse is varied between two or more discrete intervals of the initial modulated pulse.

6. The method of claim 1, wherein one or more secondary pulses are transmitted after the initial modulated pulse and wherein the one or more secondary pulses induce a refocusing of the transverse magnetization excited by the initial modulated pulse.

7. The method of claim 6, wherein a refocused transverse magnetization is recorded by the at least one receiving device.

8. The method of claim 1, further comprising:
performing a plurality of acquisition sequences between which a frequency, phase, amplitude modulation, or maximum amplitude of the initial modulated pulse is varied such that the transverse magnetization component is excited over differing subvolumes of the subsurface fluid between the plurality of acquisition sequences; and
wherein, for each respective acquisition sequence of the plurality of acquisition sequences, a respective NMR signal associated with a respective transverse magnetization component excited by a respective initial modulated pulse is recorded on the at least one receiving device.

9. The method of claim 8, further comprising combining recorded NMR signals from each respective acquisition sequence of the plurality of acquisition sequences in a mathematic inversion or linear combination to determine a distribution of subsurface fluids, their abundance, and their NMR relaxation time parameters as a function of depth.

10. The method of claim 1, further comprising deploying multiple receiving devices inside or nearby the surface coil such that the receiving devices are sensitive to NMR signals emitted by different subvolumes of the subsurface fluid.

11. The method of claim 10, further comprising combining NMR signals received at the multiple receiving devices in a mathematic inversion or linear combination to determine a 2D or 3D distribution of subsurface fluids, their abundance, and their NMR relaxation time parameters as a function of position.

12. The method of claim 1, further comprising performing a plurality of acquisition sequences between which the surface coil is moved to different locations.

13. The method of claim 1, further comprising performing a plurality of acquisition sequences, and combining recorded NMR signals from each of the acquisition sequences to determine a 2D or 3D distribution of subsurface fluids, their abundance, and their NMR relaxation time parameters as a function of position.

14. The method of claim 1, wherein at least two acquisition sequences are performed, and wherein:
for a first acquisition sequence, a first initial modulated pulse is a first adiabatic pulse and the frequency of the first adiabatic pulse is swept from below resonance upward to an on-resonance condition; and
for a second acquisition sequence, a second initial modulated pulse is a second adiabatic pulse and the frequency of the second adiabatic pulse is swept from above resonance downward to an on-resonance condition.

15. The method of claim 14, further comprising performing a linear combination of the at least two acquisition sequences in order to cancel one component of magnetization excited by the at least two acquisition sequences and to preserve another component of the magnetization excited by the at least two acquisition sequences.

16. The method of claim 1, further comprising controlling the current amplitude I(t) of the initial modulated pulse by adjusting an offset between a frequency of a driving signal and a resonant frequency of the surface coil.

17. The method of claim 1, further comprising using recorded NMR signals to estimate information about relaxation times $T_1$ and $T_2^*$, $T_2$ and $T_D$ of the subsurface fluid as a function of position.

18. The method of claim 1, further comprising using recorded NMR signals to estimate a physical property of a subsurface Earth or an engineered material, the physical property including one or more of a geologic, hydrogeologic, mineralogic, or biogeologic property.

19. The method of claim 1, further comprising controlling the current amplitude I(t) of the initial modulated pulse by varying, by a measurement control module in a surface NMR acquisition apparatus, a duty cycle of an Alternating Current (AC) switched current from a Direct Current (DC) power supply.

20. The method of claim 1, further comprising controlling the current amplitude I(t) of the initial modulated pulse by switching, by a measurement control module in a surface NMR acquisition apparatus, a transmitting circuit between two or more power supplies with different bus voltages.

21. The method of claim 1, further comprising controlling the current amplitude I(t) of the initial modulated pulse by switching, by a measurement control module in a surface NMR acquisition apparatus, an impedance element to selectively couple the impedance element within a transmitting circuit in the surface NMR acquisition apparatus.

22. A surface Nuclear Magnetic Resonance (NMR) measurement apparatus configured to generate at least one acquisition sequence, the surface NMR measurement apparatus comprising:

a controller; and one or more NMR surface coils for use on a ground surface where the Earth's magnetic field provides a static background magnetic field for measurements with the NMR surface coils;

wherein the controller is configured to cause at least one NMR surface coil of the one or more NMR surface coils to generate at least one acquisition sequence comprising at least one initial modulated pulse, the acquisition sequence comprising:

the initial modulated pulse transmitted with the at least one NMR surface coil, wherein at least the amplitude of the initial modulated pulse is varied during the initial modulated pulse, and wherein the initial modulated pulse excites a transverse magnetization component within a subsurface fluid;

wherein the amplitude of the initial modulated pulse is varied during the initial modulated pulse by controlling a current amplitude $I(t)$ of the initial modulated pulse in the surface coil; and a recording device configured to record an NMR signal associated with the transverse magnetization component excited by the initial modulated pulse.

* * * * *